US007220721B1

(12) United States Patent
Beeley et al.

(10) Patent No.: US 7,220,721 B1
(45) Date of Patent: May 22, 2007

(54) EXENDIN AGONIST PEPTIDES

(75) Inventors: Nigel R. Beeley, Solana Beach, CA (US); Kathryn S. Prickett, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/554,531

(22) PCT Filed: Nov. 13, 1998

(86) PCT No.: PCT/US98/24273

§ 371 (c)(1),
(2), (4) Date: Aug. 8, 2000

(87) PCT Pub. No.: WO99/25728

PCT Pub. Date: May 27, 1999

Related U.S. Application Data

(60) Provisional application No. 60/066,029, filed on Nov. 14, 1997.

(51) Int. Cl.
*A61K 38/16* (2006.01)
*A61K 38/00* (2006.01)
*A61K 38/02* (2006.01)
*C07K 14/00* (2006.01)
*C07K 2/00* (2006.01)
*C07K 1/00* (2006.01)

(52) U.S. Cl. .............................. 514/12; 514/2; 530/300; 530/324; 530/333

(58) Field of Classification Search ................ 530/855, 530/324; 514/12, 866
See application file for complete search history.

(56) References Cited

U.S. PATENT DOCUMENTS

| 5,424,286 A | 6/1995 | Eng |
| 6,506,724 B1 * | 1/2003 | Hiles et al. ..................... 514/2 |
| 6,924,264 B1 * | 8/2005 | Prickett et al. ................. 514/2 |

FOREIGN PATENT DOCUMENTS

| AU | 723694 | 1/1998 |
| WO | WO 9746584 A1 * | 12/1997 |
| WO | WO 98/05351 | 2/1998 |
| WO | WO 98/30231 | 7/1998 |
| WO | WO 99/07404 | 2/1999 |

OTHER PUBLICATIONS

D'Alessio, et al., "Elimination of the action of glucagon-like peptide 1 causes an impairment of glucose tolerance after nutrient ingestion by healthy baboons," *J. Clin. Invest.* 97:133-138 (1996).
Daniel, et al.., "Use of Glucagon in the Treatment of Acute Diverticultis," *Br. Med. J.*, 3:720 (1974).

Eissele, et al., "Rat gastric somatostatin and gastrin release: Interactions of exendin-4 and truncated glucagon-like peptide-1 (GLP-1) amide," *Life Sci.* 55:629-634 (1994).
Eng, et al., "Isolation and characterization of exendin-4, an exendin-3 analogue, from heloderma suspectum venom," *J. Biol. Chem.* 267:7402-7405 (1992).
Eng, et al., "Purification and structure of exendin-3, a new pancreatic secretagogue isolated from heloderma horridum venom," *J. Biol. Chem.* 265:20259-20262 (1990).
Glauser, et al., "Intravenous Glucagon in the Management of Esophageal Food Obstruction," *J. Am. Coll. Emergency Physns.*, 8:228 (1979).
Goke, et al., "Exendin-4 is a high potency agonist and truncated exendin-(9-39)-amide an antagonist at the glucagon-like peptide 1-(7-36)- amide receptor of insulin-secreting β-cells," *J. Biol. Chem.* 268:19650-19655 (1993).
Malhotra, et al., "Exendin-4, a new peptide from Heloderma suspectum venom, potentiates cholecystokinin-induced amylase release from rat pancreatic acini," *Regulatory Peptides* 41:149-156 (1992).
O'Halloran, et al., "Glucagon-like peptide-1 (7-36)-NH$_2$: A physiological inhibitor of gastric acid secretion in man," *J. Endocrinol.* 126(1):169-173 (1990).
Orskov, et al., "Biological effects and metabolic rates of glucagon-like peptide-1 7-36 amide and glucagonlike peptide-1 7-37 in healthy subjects are indistinguishable," *Diabetes* 42:658-661 (1993).
Raufman, et al., "Truncated glucagon-like peptide-1 interacts with exendin receptors on dispersed acini from guinea pig pancreas," *J. Biol. Chem.* 267:21432-21437 (1992).
Scarpignato, et al, "Action of Caerulein on Gastric Emptying of the Conscious Rat," *Arch. int. Pharmacodyn.* 246:286-294 (1980).
Schepp, et al., "Exendin-4 and exendin-(9-39) NH2: Agonist and antagonist, respectively, at the rat parietal cell receptor for glucagon-like peptide-1-(7-36)NH2," *Eur. J. Pharmacol.* 269:183-191 (1994).
Schjoldager, et al., "GLP-1 (Glucagon-like peptide 1) and truncated GLP-1 fragments of human proglucagon, inhibit gastric acid secretion in humans," *Dig Dis. Sci.* 34(5):703-708 (1989).
Singh, et al., "Use of 125I-[Y39] exendin-4 to characterize exendin receptors on dispersed pancreatic acini and gastric chief cells from guinea pig," *Regul. Pept.* 53:47-59 (1994).
Stower, et al., "A Trial of Glucagon in the Treatment of Painful Biliary Tract Disease," *Br. J. Surg.*, 69:591-592 (1982).
Thorens, "Expression cloning of the pancreatic β cell receptor for the gluco-incretin hormone glucagon-like peptide 1," *Proc. Natl. Acad. Sci.* USA 89:8641-8645 (1992).
Wettergren, et al, "Truncated GLP-1 (Proglucagon 78-107-Amide) Inhibits Gastric and Pancreatic Functions in Man," *Digestive Diseases and Sciences*, 38(4):665-673 (1993).
Willms, et al., "Gastric emptying, glucose responses, and insulin secretion after a liquid test meal: Effects of exogenous glucagon-like peptide-1 (GLP-1)-(7-36) amide in type 2 (Noninsulin-dependent) diabetic patients," *J. Clin. Endocrinol. Metab.* 81(1):327-332 (1996).

\* cited by examiner

*Primary Examiner*—Cecilia J. Tsang
*Assistant Examiner*—Andrew D. Kosar

(57) ABSTRACT

Novel exendin agonist compounds are provided. These compounds are useful in treating diabetes and conditions which would be benefited by lowering plasma glucose or delaying and/or slowing gastric emptying.

75 Claims, 11 Drawing Sheets

EXENDIN-3

```
His Ser Asp Gly Thr Phe Thr Ser Asp Leu Ser Lys Gln Met Glu Glu
1            5                   10                  15
Glu Ala Val Arg Leu Phe Ile Glu Trp Leu Lys Asn Gly Gly Pro Ser
            20                  25                  30
Ser Gly Ala Pro Pro Pro Ser-NH₂
            35
```

FIGURE 1

EXENDIN-4

His Gly Glu Gly Thr Phe Thr Ser Asp Leu Ser Lys Gln Met Glu Glu
                  5                  10                 15
Glu Ala Val Arg Leu Phe Ile Glu Trp Leu Lys Asn Gly Gly Pro Ser
            20              25                  30
Ser Gly Ala Pro Pro Pro Ser-NH$_2$
            35

FIGURE 2

GLP-1 (GLP-1(7-36)NH₂)

His Ala Glu Gly Thr Phe Thr Ser Asp Val Ser Ser Tyr Leu Glu Gly
              5                   10                      15
Gln Ala Ala Lys Glu Phe Ile Ala Trp Leu Val Lys Gly Arg-NH₂
              20              25                  30

FIGURE 3

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|
| Compound 1 | Ala | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | | |
| Compound 2 | His | Gly | Ala | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | | |
| Compound 3 | His | Gly | Glu | Ala | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | | |
| Compound 4 | His | Gly | Glu | Gly | Ala | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | | |
| Compound 5 | Ala | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 6 | His | Gly | Ala | Ala | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 7 | His | Gly | Glu | Ala | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 8 | His | Gly | Glu | Gly | Thr | Phe | Thr | Ser | Ala | Ala | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 9 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 10 | Ala | Ala | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | NH2 | | | | | | | | | | |
| Compound 11 | Ala | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 12 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 13 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 14 | Ala | Gly | Asp | Gly | Ala | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 15 | Ala | Gly | Asp | Gly | Ala | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 16 | Ala | Gly | Asp | Gly | Thr | Nala | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 17 | Ala | Gly | Asp | Gly | Thr | Nala | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 18 | Ala | Gly | Asp | Gly | Thr | Phe | Ser | Ser | Asp | Leu | Ser | Lys | Gln | Leu | Glu | Glu | Glu | Ala | Val | Arg | Leu | Phe | Ile | Glu | Trp | Leu | Lys | Asn | NH2 | | | | | | | | | | |
| Compound 19 | Ala | Gly | Asp | Gly | Thr | Phe | Ser | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 20 | Ala | Gly | Asp | Gly | Thr | Phe | Thr | Ala | Asp | Leu | Ser | Lys | Gln | Leu | Glu | Glu | Glu | Ala | Val | Arg | Leu | Phe | Ile | Glu | Trp | Leu | Lys | Asn | NH2 | | | | | | | | | | |
| Compound 21 | Ala | Gly | Asp | Gly | Thr | Phe | Thr | Ala | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 22 | Ala | Gly | Asp | Gly | Thr | Phe | Thr | Ser | Ala | Ala | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 23 | Ala | Gly | Asp | Gly | Thr | Phe | Thr | Ser | Glu | Pgly | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 24 | Ala | Gly | Asp | Gly | Thr | Phe | Thr | Ser | Glu | Leu | Ala | Lys | Gln | Met | Glu | Glu | Glu | Ala | Val | Arg | Leu | Phe | Ile | Glu | Trp | Leu | Lys | Asn | NH2 | | | | | | | | | | |
| Compound 25 | Ala | Gly | Asp | Gly | Thr | Phe | Thr | Ser | Asp | Leu | Ala | Lys | Gln | Met | Glu | Glu | Glu | Ala | Val | Arg | Leu | Phe | Ile | Glu | Trp | Leu | Lys | Asn | NH2 | | | | | | | | | | |
| Compound 26 | Ala | Gly | Asp | Gly | Thr | Phe | Thr | Ser | Asp | Leu | Ser | Ala | Gln | Met | Glu | Glu | Glu | Ala | Val | Arg | Leu | Phe | Ile | Glu | Trp | Leu | Lys | Asn | NH2 | | | | | | | | | | |
| Compound 27 | Ala | Gly | Asp | Gly | Thr | Phe | Thr | Ser | Asp | Leu | Ser | Ala | Gln | Met | Glu | Glu | Glu | Ala | Val | Arg | Leu | Phe | Ile | Glu | Phe | Leu | Lys | Asn | NH2 | | | | | | | | | | |
| Compound 28 | Ala | Gly | Asp | Gly | Thr | Phe | Thr | Ser | Asp | Leu | Ser | Lys | Ala | Met | Glu | Glu | Glu | Ala | Val | Arg | Leu | Phe | Ile | Glu | Trp | Leu | Lys | Asn | NH2 | | | | | | | | | | |
| Compound 29 | Ala | Gly | Asp | Gly | Thr | Phe | Thr | Ser | Asp | Leu | Ser | Lys | Ala | Leu | Glu | Glu | Glu | Ala | Val | Arg | Leu | Phe | Ile | Glu | Phe | Leu | Lys | Asn | NH2 | | | | | | | | | | |
| Compound 30 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | NH2 | | | | | | | | | | |
| Compound 31 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | NH2 | | | | | | | | | | |
| Compound 32 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | NH2 | | | | | | | | | | |
| Compound 33 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | NH2 | | | | | | | | | | |
| Compound 34 | Ala | Gly | Asp | Gly | Thr | Phe | Thr | Ser | Asp | Leu | Ser | Lys | Ala | Leu | Glu | Glu | Glu | Ala | Val | Arg | Leu | Phe | Ile | Glu | Trp | Leu | Lys | Asn | NH2 | | | | | | | | | | |
| Compound 35 | Ala | Gly | Asp | Gly | Thr | Phe | Thr | Ser | Asp | Leu | Ser | Lys | Ala | Leu | Glu | Glu | Glu | Ala | Val | Arg | Leu | Phe | Ile | Glu | Phe | Leu | Lys | Asn | NH2 | | | | | | | | | | |

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|
| Compound 36 | Ala | Gly | Asp | Gly | Thr | Phe | Thr | Ser | Asp | Leu | Ser | Lys | Gln | Ala | Glu | Glu | Glu | Ala | Val | Arg | Leu | Phe | Ile | Glu | Trp | Leu | Lys | Asn | NH2 | | | | | | | | | | |
| Compound 37 | Ala | Gly | Asp | Gly | Thr | Phe | Thr | Ser | Asp | Leu | Ser | Lys | Gln | Ala | Glu | Glu | Glu | Ala | Val | Arg | Leu | Phe | Ile | Glu | Phe | Leu | Lys | Asn | NH2 | | | | | | | | | | |
| Compound 38 | Ala | Gly | Asp | Gly | Thr | Phe | Thr | Ser | Asp | Leu | Ser | Lys | Gln | pGly | Glu | Glu | Glu | Ala | Val | Arg | Leu | Phe | Ile | Glu | Trp | Leu | Lys | Asn | NH2 | | | | | | | | | | |
| Compound 39 | Ala | Gly | Asp | Gly | Thr | Phe | Thr | Ser | Asp | Leu | Ser | Lys | Gln | pGly | Glu | Glu | Glu | Ala | Val | Arg | Leu | Phe | Ile | Glu | Phe | Leu | Lys | Asn | NH2 | | | | | | | | | | |
| Compound 40 | Ala | Gly | Asp | Gly | Thr | Phe | Thr | Ser | Asp | Leu | Ser | Lys | Gln | Met | Ala | Ala | Glu | Ala | Val | Arg | Leu | Phe | Ile | Glu | Trp | Leu | Lys | Asn | NH2 | | | | | | | | | | |
| Compound 41 | Ala | Gly | Asp | Gly | Thr | Phe | Thr | Ser | Asp | Leu | Ser | Lys | Gln | Leu | Ala | Ala | Glu | Ala | Val | Arg | Leu | Phe | Ile | Glu | Phe | Leu | Lys | Asn | NH2 | | | | | | | | | | |
| Compound 42 | Ala | Gly | Asp | Gly | Thr | Phe | Thr | Ser | Asp | Leu | Ser | Lys | Gln | Met | Glu | Ala | Ala | Ala | Val | Arg | Leu | Phe | Ile | Glu | Trp | Leu | Lys | Asn | NH2 | | | | | | | | | | |
| Compound 43 | Ala | Gly | Asp | Gly | Thr | Phe | Thr | Ser | Asp | Leu | Ser | Lys | Gln | Leu | Glu | Ala | Ala | Ala | Val | Arg | Leu | Phe | Ile | Glu | Phe | Leu | Lys | Asn | NH2 | | | | | | | | | | |
| Compound 44 | Ala | Gly | Asp | Gly | Thr | Phe | Thr | Ser | Asp | Leu | Ser | Lys | Gln | Met | Glu | Glu | Ala | Ala | Val | Arg | Leu | Phe | Ile | Glu | Trp | Leu | Lys | Asn | NH2 | | | | | | | | | | |
| Compound 45 | Ala | Gly | Asp | Gly | Thr | Phe | Thr | Ser | Asp | Leu | Ser | Lys | Gln | Leu | Glu | Glu | Ala | Ala | Val | Arg | Leu | Phe | Ile | Glu | Phe | Leu | Lys | Asn | NH2 | | | | | | | | | | |
| Compound 46 | Ala | Gly | Asp | Gly | Thr | Phe | Thr | Ser | Asp | Leu | Ser | Lys | Gln | Met | Glu | Glu | Glu | Ala | Ala | Arg | Leu | Phe | Ile | Glu | Trp | Leu | Lys | Asn | NH2 | | | | | | | | | | |
| Compound 47 | Ala | Gly | Asp | Gly | Thr | Phe | Thr | Ser | Asp | Leu | Ser | Lys | Gln | Leu | Glu | Glu | Glu | Ala | Ala | Arg | Leu | Phe | Ile | Glu | Phe | Leu | Lys | Asn | NH2 | | | | | | | | | | |
| Compound 48 | Ala | Gly | Asp | Gly | Thr | Phe | Thr | Ser | Asp | Leu | Ser | Lys | Gln | Met | Glu | Glu | Glu | Ala | Val | Ala | Leu | Phe | Ile | Glu | Trp | Leu | Lys | Asn | NH2 | | | | | | | | | | |
| Compound 49 | Ala | Gly | Asp | Gly | Thr | Phe | Thr | Ser | Asp | Leu | Ser | Lys | Gln | Leu | Glu | Glu | Glu | Ala | Val | Ala | Leu | Phe | Ile | Glu | Phe | Leu | Lys | Asn | NH2 | | | | | | | | | | |
| Compound 50 | Ala | Gly | Asp | Gly | Thr | Phe | Thr | Ser | Asp | Leu | Ser | Lys | Gln | Met | Glu | Glu | Glu | Ala | Val | Arg | Ala | Phe | Ile | Glu | Trp | Leu | Lys | Asn | NH2 | | | | | | | | | | |
| Compound 51 | Ala | Gly | Asp | Gly | Thr | Phe | Thr | Ser | Asp | Leu | Ser | Lys | Gln | Leu | Glu | Glu | Glu | Ala | Val | Arg | Ala | Phe | Ile | Glu | Phe | Leu | Lys | Asn | NH2 | | | | | | | | | | |
| Compound 52 | Ala | Gly | Asp | Gly | Thr | Phe | Thr | Ser | Asp | Leu | Ser | Lys | Gln | Met | Glu | Glu | Glu | Ala | Val | Arg | Leu | Nala | Ile | Glu | Trp | Leu | Lys | Asn | NH2 | | | | | | | | | | |
| Compound 53 | Ala | Gly | Asp | Gly | Thr | Phe | Thr | Ser | Asp | Leu | Ser | Lys | Gln | Leu | Glu | Glu | Glu | Ala | Val | Arg | Leu | Nala | Ile | Glu | Phe | Leu | Lys | Asn | NH2 | | | | | | | | | | |
| Compound 54 | Ala | Gly | Asp | Gly | Thr | Phe | Thr | Ser | Asp | Leu | Ser | Lys | Gln | Met | Glu | Glu | Glu | Ala | Val | Arg | Leu | Phe | Val | Glu | Trp | Leu | Lys | Asn | NH2 | | | | | | | | | | |
| Compound 55 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Val | Glu | Phe | Leu | Lys | Asn | NH2 | | | | | | | | | | |
| Compound 56 | Ala | Gly | Asp | Gly | Thr | Phe | Thr | Ser | Asp | Leu | Ser | Lys | Gln | Met | Glu | Glu | Glu | Ala | Val | Arg | Leu | Phe | lGly | Glu | Trp | Leu | Lys | Asn | NH2 | | | | | | | | | | |
| Compound 57 | Ala | Gly | Asp | Gly | Thr | Phe | Thr | Ser | Asp | Leu | Ser | Lys | Gln | Leu | Glu | Glu | Glu | Ala | Val | Arg | Leu | Phe | lGly | Glu | Phe | Leu | Lys | Asn | NH2 | | | | | | | | | | |
| Compound 58 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Asp | Trp | Leu | Lys | Asn | NH2 | | | | | | | | | | |
| Compound 59 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Asp | Phe | Leu | Lys | Asn | NH2 | | | | | | | | | | |
| Compound 60 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Ala | Leu | Lys | Asn | NH2 | | | | | | | | | | |
| Compound 61 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Glu | Ala | Leu | Lys | Asn | NH2 | | | | | | | | | | |
| Compound 62 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Trp | Ala | Lys | Asn | NH2 | | | | | | | | | | |
| Compound 63 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Glu | Phe | Ala | Lys | Asn | NH2 | | | | | | | | | | |
| Compound 64 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Ala | Asn | NH2 | | | | | | | | | | |
| Compound 65 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Ala | Asn | NH2 | | | | | | | | | | |
| Compound 66 | Ala | Gly | Asp | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Ala | NH2 | | | | | | | | | | |
| Compound 67 | Ala | Gly | Asp | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Ala | NH2 | | | | | | | | | | |
| Compound 68 | Ala | Gly | Ala | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Gly | Ala | Pro | Pro | Pro | Pro | NH2 |
| Compound 69 | His | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | Gly | Gly | Pro | Ser | Gly | Ala | Pro | Pro | Pro | Pro | NH2 |
| Compound 70 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Gly | Ala | Pro | Pro | Pro | Pro | NH2 |
| Compound 71 | His | Gly | Glu | Gly | Thr | Phe | Thr | Ser | Ala | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Gly | Ala | Pro | NH2 | | | |

| Amino Acid Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|
| Compound 72 | Ala | Gly | Glu | Gly | Thr | Phe | Thr | Ser | Asp | Ala | Ser | Lys | Gln | Leu | Glu | Glu | Glu | Ala | Val | Arg | Leu | Phe | Ile | Glu | Phe | Leu | Lys | Asn | Gly | Gly | Pro | Ser | Ser | Gly | Ala | Pro | NH2 | | |
| Compound 73 | Ala | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | NH2 | | | |
| Compound 74 | His | Gly | Ala | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | Gly | Gly | Pro | Ser | Ser | Gly | Ala | NH2 | | | |
| Compound 75 | His | Gly | Glu | Ala | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | Gly | Gly | Pro | Ser | Ser | Gly | NH2 | | | | |
| Compound 76 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | | | | | |
| Compound 77 | Ala | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Trp | Leu | Lys | Asn | Gly | Gly | Pro | Ser | Ser | Gly | Ala | | | | |
| Compound 78 | His | Gly | Ala | Gly | Thr | Phe | Thr | Ser | Asp | Leu | Ser | Lys | Gln | Met | Glu | Glu | Glu | Ala | Val | Arg | Leu | Phe | Ile | Glu | Phe | Leu | Lys | Asn | Gly | Gly | Pro | Ser | NH2 | | | | | | |
| Compound 79 | His | Gly | Glu | Ala | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | NH2 | | | | | | | |
| Compound 80 | His | Gly | Glu | Gly | Thr | Phe | Thr | Ser | Ala | Leu | Ser | Lys | Gln | Leu | Glu | Glu | Glu | Ala | Val | Arg | Leu | Phe | Ile | Glu | Phe | Leu | Lys | Asn | Gly | NH2 | | | | | | | | | |
| Compound 81 | Ala | Gly | Glu | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | Gly | iPro | Ser | Ser | Gly | Ala | iPro | iPro | iPro | NH2 |
| Compound 82 | His | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | iPro | iPro | iPro | NH2 |
| Compound 83 | His | Gly | Glu | Ala | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Nme | Ser | Ser | Gly | Ala | Nme | Nme | NH2 | |
| Compound 84 | His | Gly | Glu | Gly | Thr | Phe | Thr | Ser | Ala | Leu | Ser | Lys | Gln | Met | Glu | Glu | Glu | Ala | Val | Arg | Leu | Phe | Ile | Glu | Trp | Leu | Lys | Asn | Gly | Gly | hPro | Ser | Ser | Gly | Ala | hPro | NH2 | | |
| Compound 85 | Ala | Gly | Ala | Ala | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | NH2 | | | |
| Compound 86 | His | Gly | Glu | Gly | Thr | Phe | Thr | Ser | Asp | Leu | Ser | Lys | Gln | Met | Glu | Glu | Glu | Ala | Val | Arg | Asp | Leu | Phe | Ile | Glu | Trp | Leu | Lys | Asn | Gly | NH2 | | | | | | | | |
| Compound 87 | His | Gly | Asp | Ala | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | Pro | Pro | Ser | NH2 |
| Compound 88 | Ala | Gly | Glu | Gly | Thr | Phe | Thr | Ser | Asp | Leu | Ser | Lys | Gln | Met | Glu | Glu | Glu | Ala | Val | Arg | Leu | Phe | Ile | Glu | Trp | Leu | Lys | Asn | Gly | Gly | Pro | Ser | Ser | Gly | Ala | Pro | Pro | Ser | NH2 |
| Compound 89 | Ala | Gly | Ala | Gly | Thr | Phe | Thr | Ser | Asp | Leu | Ser | Lys | Gln | Leu | Glu | Glu | Glu | Ala | Val | Arg | Leu | Phe | Ile | Glu | Phe | Leu | Lys | Asn | Gly | Gly | Pro | Ser | | | | | | | |

Cmp
No.

90  4-Imidazolylpropionyl-Gly Glu Gly Thr Phe Thr Ser Ala Leu
    Ser Lys Gln Met Glu Glu Glu Ala Val Arg Leu Phe Ile Glu Trp
    Leu Lys-NH$^\varepsilon$octanoyl Asn-$NH_2$ [SEQ. ID. NO. 95]

91  4-Imidazolylpropionyl-Gly Glu Gly Thr Phe Thr Ser Ala Leu
    Ser Lys Gln Leu Glu Glu Glu Ala Val Arg Leu Phe Ile Glu Phe
    Leu Lys-NH$^\varepsilon$octanoyl Asn-$NH_2$ [SEQ. ID. NO. 96]

92  4-Imidazolylpropionyl-Gly Glu Gly Thr Phe Thr Ser Ala Leu
    Ser Lys Gln Met Glu Glu Glu Ala Val Arg Leu Phe Ile Glu Trp
    Leu Lys-NH$^\varepsilon$octanoyl Asn Gly Gly-$NH_2$ [SEQ. ID. NO. 97]

93  4-Imidazolylpropionyl-Gly Glu Gly Thr Phe Thr Ser Ala Leu
    Ser Lys Gln Leu Glu Glu Glu Ala Val Arg Leu Phe Ile Glu Phe
    Leu Lys-NH$^\varepsilon$octanoyl Asn Gly Gly-$NH_2$ [SEQ. ID. NO. 98]

94  4-Imidazolylpropionyl-Gly Glu Gly Thr Phe Thr Ser Ala Leu
    Ser Lys Gln Met Glu Glu Glu Ala Val Arg Leu Phe Ile Glu Trp
    Leu Asn Lys-NH$^\varepsilon$octanoyl-$NH_2$ [SEQ. ID. NO. 99]

95  4-Imidazolylpropionyl-Gly Glu Gly Thr Phe Thr Ser Ala Leu
    Ser Lys Gln Leu Glu Glu Glu Ala Val Arg Leu Phe Ile Glu Phe
    Leu Asn Lys-NH$^\varepsilon$octanoyl-$NH_2$ [SEQ. ID. NO. 100]

Page 1

FIGURE 7

96    4-Imidazolylpropionyl-Gly Glu Gly Thr Phe Thr Ser Ala Leu Ser Lys Gln Met Glu Glu Glu Ala Val Arg Leu Phe Ile Glu Trp Leu Asn Lys-NH$^\varepsilon$octanoyl Gly Gly-NH$_2$ [SEQ. ID. NO. 101]

97    4-Imidazolylpropionyl-Gly Glu Gly Thr Phe Thr Ser Ala Leu Ser Lys Gln Leu Glu Glu Glu Ala Val Arg Leu Phe Ile Glu Phe Leu Asn Lys-NH$^\varepsilon$octanoyl Gly Gly-NH$_2$ [SEQ. ID. NO. 102]

98    Ala Gly Glu Gly Thr Phe Thr Ser Asp Leu Ser Lys Gln Met Glu Glu Glu Ala Val Arg Leu Phe Ile Glu Trp Leu Lys-NH$^\varepsilon$octanoyl Asn-NH$_2$ [SEQ. ID. NO. 103]

99    Ala Gly Glu Gly Thr Phe Thr Ser Asp Leu Ser Lys Gln Leu Glu Glu Glu Ala Val Arg Leu Phe Ile Glu Phe Leu Lys-NH$^\varepsilon$octanoyl Asn-NH$_2$ [SEQ. ID. NO. 104]

100    Ala Gly Glu Gly Thr Phe Thr Ser Asp Leu Ser Lys Gln Met Glu Glu Glu Ala Val Arg Leu Phe Ile Glu Trp Leu Lys-NH$^\varepsilon$octanoyl Asn Gly Gly-NH$_2$ [SEQ. ID. NO. 105]

101    Ala Gly Glu Gly Thr Phe Thr Ser Asp Leu Ser Lys Gln Leu Glu Glu Glu Ala Val Arg Leu Phe Ile Glu Phe Leu Lys-NH$^\varepsilon$octanoyl Asn Gly Gly-NH$_2$ [SEQ. ID. NO. 106]

102    Ala Gly Glu Gly Thr Phe Thr Ser Asp Leu Ser Lys Gln Met Glu Glu Glu Ala Val Arg Leu Phe Ile Glu Trp Leu Asn Lys-NH$^\varepsilon$octanoyl-NH$_2$ [SEQ. ID. NO. 107]

Page 2

FIGURE 7

103 Ala Gly Glu Gly Thr Phe Thr Ser Asp Leu Ser Lys Gln Leu Glu
Glu Glu Ala Val Arg Leu Phe Ile Glu Phe Leu Asn Lys-
NH$^\varepsilon$octanoyl-$NH_2$ [SEQ. ID. NO. 108]

104 Ala Gly Glu Gly Thr Phe Thr Ser Asp Leu Ser Lys Gln Met Glu
Glu Glu Ala Val Arg Leu Phe Ile Glu Trp Leu Asn Lys-
NH$^\varepsilon$octanoyl Gly Gly-$NH_2$ [SEQ. ID. NO. 109]

105 Ala Gly Glu Gly Thr Phe Thr Ser Asp Leu Ser Lys Gln Leu Glu
Glu Glu Ala Val Arg Leu Phe Ile Glu Phe Leu Asn Lys-
NH$^\varepsilon$octanoyl Gly Gly-$NH_2$ [SEQ. ID. NO. 110]

SEQUENCE LISTING

```
<160> NUMBER OF SEQ ID NOS: 110

<210> SEQ ID NO 1
<211> LENGTH: 39
<212> TYPE: PRT
<213> ORGANISM: Heloderma horridum
<220> FEATURE:
<223> OTHER INFORMATION: c-term amidation

<400> SEQUENCE: 1

His Ser Asp Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 2
<211> LENGTH: 39
<212> TYPE: PRT
<213> ORGANISM: Heloderma suspectum
<220> FEATURE:
<223> OTHER INFORMATION: c-term amidation

<400> SEQUENCE: 2

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 3
<211> LENGTH: 30
<212> TYPE: PRT
<213> ORGANISM: Homo sapiens
<220> FEATURE:
<223> OTHER INFORMATION: c-term amidation

<400> SEQUENCE: 3

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 4
<211> LENGTH: 39
<212> TYPE: PRT
```

```
<213> ORGANISM: Artificial Sequence
<220> FEATURE:
<223> OTHER INFORMATION: Description of Artificial Sequence: Exendin
      agonist formula peptide
<220> FEATURE:
<223> OTHER INFORMATION: c-term may be amidated
<220> FEATURE:
<221> NAME/KEY: MOD_RES
<222> LOCATION: (1)
<223> OTHER INFORMATION: His, Arg, Tyr, Ala, Norval, Val or Norleu
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (4)
<223> OTHER INFORMATION: Ala, Norval, Val, Norleu or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Ala, Norval, Val, Norleu, Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
```

```
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine, tert-butylglycine
    or Met
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp, Phe, Tyr or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (31)
<223> OTHER INFORMATION: Pro, homoproline, 3Hyp, 4Hyp, thioproline,
    N-alkylglycine, N-alkylpentylglycine or N-alkylalanine
<220> FEATURE:
<221> NAME/KEY: MOD_RES
<222> LOCATION: (36)..(38)
<223> OTHER INFORMATION: Pro, homoproline, 3Hyp, 4Hyp, thioproline,
    N-alkylglycine, N-alkylpentylglycine or N-alkylalanine
<220> FEATURE:
<221> NAME/KEY: MOD_RES
<222> LOCATION: (39)
<223> OTHER INFORMATION: Ser or Tyr
<220> FEATURE:
<223> OTHER INFORMATION: provided that no more than three of Xaa3, Xaa4,
    Xaa5, Xaa6, Xaa8, Xaa9, Xaa10, Xaa11, Xaa12, Xaa13, Xaa14, Xaa15,
    Xaa16, Xaa17, Xaa19, Xaa20, Xaa21, Xaa24, Xaa25, Xaa26,
    Xaa27 and Xaa28 are Ala
<220> FEATURE:
<223> OTHER INFORMATION: provided also that, if Xaa1 is His, Arg or Tyr,
    then at least one of Xaa3, Xaa4 and Xaa9 is Ala
<220> FEATURE:
<223> OTHER INFORMATION: this peptide may encompass 28-39 residues,
    wherein residues 1-28 are constant and residues 29-39 may vary in
    length according to the specification as filed; see specification
    for detailed description of substitutions and preferred
    embodiments

<400> SEQUENCE: 4

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Gly Gly Xaa Ser
             20                  25                  30

Ser Gly Ala Xaa Xaa Xaa Xaa
         35

<210> SEQ ID NO 5
<211> LENGTH: 28
```

-continued

```
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 5

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 6

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 7

His Gly Glu Ala Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 8

His Gly Glu Gly Thr Phe Thr Ser Ala Leu Ser Lys Gln Leu Glu Glu
 1               5                  10                  15

Glu Ala Val Arg Leu Phe Ile Glu Phe Leu Lys Asn
            20                  25

<210> SEQ ID NO 9
<211> LENGTH: 28
<212> TYPE: PRT
<213> ORGANISM: Artificial Sequence
<220> FEATURE:
```

```
<223> OTHER INFORMATION: Description of Artificial Sequence: Exendin
      agonist
<220> FEATURE:
<223> OTHER INFORMATION: c-term amidation

<400> SEQUENCE: 9

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 10

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 11

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 12

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
```

<223> OTHER INFORMATION: c-term amidation

<400> SEQUENCE: 13

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 14

Ala Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 15

Ala Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 16

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 17

Ala Gly Asp Gly Thr Phe Thr Ser Asp Leu Ser Lys Gln Leu Glu Glu
 1               5                   10                  15

Glu Ala Val Arg Leu Phe Ile Glu Phe Leu Lys Asn
             20                  25

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 18

Ala Gly Asp Gly Ala Phe Thr Ser Asp Leu Ser Lys Gln Met Glu Glu
 1               5                   10                  15

Glu Ala Val Arg Leu Phe Ile Glu Trp Leu Lys Asn
             20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 19

Ala Gly Asp Gly Ala Phe Thr Ser Asp Leu Ser Lys Gln Leu Glu Glu
 1               5                   10                  15

Glu Ala Val Arg Leu Phe Ile Glu Phe Leu Lys Asn
             20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (6)
<223> OTHER INFORMATION: naphthylalanine

<400> SEQUENCE: 20

Ala Gly Asp Gly Thr Xaa Thr Ser Asp Leu Ser Lys Gln Met Glu Glu
 1               5                   10                  15

Glu Ala Val Arg Leu Phe Ile Glu Trp Leu Lys Asn
             20                  25

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:

```
<221> NAME/KEY: MOD_RES
<222> LOCATION: (6)
<223> OTHER INFORMATION: naphthylalanine

<400> SEQUENCE: 21

Ala Gly Asp Gly Thr Xaa Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 22
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 22

Ala Gly Asp Gly Thr Phe Ser Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 23

Ala Gly Asp Gly Thr Phe Ser Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 24

Ala Gly Asp Gly Thr Phe Thr Ala Asp Leu Ser Lys Gln Met Glu Glu
 1               5                  10                  15

Glu Ala Val Arg Leu Phe Ile Glu Trp Leu Lys Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
```

```
<400> SEQUENCE: 25

Ala Gly Asp Gly Thr Phe Thr Ala Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 26

Ala Gly Asp Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 27

Ala Gly Asp Gly Thr Phe Thr Ser Ala Leu Ser Lys Gln Leu Glu Glu
 1               5                  10                  15

Glu Ala Val Arg Leu Phe Ile Glu Phe Leu Lys Asn
            20                  25

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 28

Ala Gly Asp Gly Thr Phe Thr Ser Glu Leu Ser Lys Gln Met Glu Glu
 1               5                  10                  15

Glu Ala Val Arg Leu Phe Ile Glu Trp Leu Lys Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 29
```

-continued

```
Ala Gly Asp Gly Thr Phe Thr Ser Glu Leu Ser Lys Gln Leu Glu Glu
1               5                   10                  15

Glu Ala Val Arg Leu Phe Ile Glu Phe Leu Lys Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 30

Ala Gly Asp Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 31

Ala Gly Asp Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (10)
<223> OTHER INFORMATION: pentlyglycine

<400> SEQUENCE: 32

Ala Gly Asp Gly Thr Phe Thr Ser Asp Xaa Ser Lys Gln Met Glu Glu
1               5                   10                  15

Glu Ala Val Arg Leu Phe Ile Glu Trp Leu Lys Asn
            20                  25

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
```

```
<222> LOCATION: (10)
<223> OTHER INFORMATION: pentlyglycine

<400> SEQUENCE: 33

Ala Gly Asp Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 34

Ala Gly Asp Gly Thr Phe Thr Ser Asp Leu Ala Lys Gln Met Glu Glu
1               5                   10                  15

Glu Ala Val Arg Leu Phe Ile Glu Trp Leu Lys Asn
            20                  25

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 35

Ala Gly Asp Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 36

Ala Gly Asp Gly Thr Phe Thr Ser Asp Leu Ser Ala Gln Met Glu Glu
1               5                   10                  15

Glu Ala Val Arg Leu Phe Ile Glu Trp Leu Lys Asn
            20                  25

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
```

```
<400> SEQUENCE: 37

Ala Gly Asp Gly Thr Phe Thr Ser Asp Leu Ser Ala Gln Leu Glu Glu
  1               5                  10                  15

Glu Ala Val Arg Leu Phe Ile Glu Phe Leu Lys Asn
            20                  25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 38

Ala Gly Asp Gly Thr Phe Thr Ser Asp Leu Ser Lys Ala Met Glu Glu
  1               5                  10                  15

Glu Ala Val Arg Leu Phe Ile Glu Trp Leu Lys Asn
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 39

Ala Gly Asp Gly Thr Phe Thr Ser Asp Leu Ser Lys Ala Leu Glu Glu
  1               5                  10                  15

Glu Ala Val Arg Leu Phe Ile Glu Phe Leu Lys Asn
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 40

Ala Gly Asp Gly Thr Phe Thr Ser Asp Leu Ser Lys Gln Ala Glu Glu
  1               5                  10                  15

Glu Ala Val Arg Leu Phe Ile Glu Trp Leu Lys Asn
            20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 41

Ala Gly Asp Gly Thr Phe Thr Ser Asp Leu Ser Lys Gln Ala Glu Glu
```

-continued

```
                1               5                  10                 15
Glu Ala Val Arg Leu Phe Ile Glu Phe Leu Lys Asn
            20                  25
```

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (14)
<223> OTHER INFORMATION: pentlyglycine

<400> SEQUENCE: 42

```
Ala Gly Asp Gly Thr Phe Thr Ser Asp Leu Ser Lys Gln Xaa Glu Glu
  1               5                  10                 15
Glu Ala Val Arg Leu Phe Ile Glu Trp Leu Lys Asn
            20                  25
```

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (14)
<223> OTHER INFORMATION: pentlyglycine

<400> SEQUENCE: 43

```
Ala Gly Asp Gly Thr Phe Thr Ser Asp Leu Ser Lys Gln Xaa Glu Glu
  1               5                  10                 15
Glu Ala Val Arg Leu Phe Ile Glu Phe Leu Lys Asn
            20                  25
```

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 44

```
Ala Gly Asp Gly Thr Phe Thr Ser Asp Leu Ser Lys Gln Met Ala Glu
  1               5                  10                 15
Glu Ala Val Arg Leu Phe Ile Glu Trp Leu Lys Asn
            20                  25
```

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:

<223> OTHER INFORMATION: c-term amidation

<400> SEQUENCE: 45

Ala Gly Asp Gly Thr Phe Thr Ser Asp Leu Ser Lys Gln Leu Ala Glu
 1               5                  10                  15

Glu Ala Val Arg Leu Phe Ile Glu Phe Leu Lys Asn
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 46

Ala Gly Asp Gly Thr Phe Thr Ser Asp Leu Ser Lys Gln Met Glu Ala
 1               5                  10                  15

Glu Ala Val Arg Leu Phe Ile Glu Trp Leu Lys Asn
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 47

Ala Gly Asp Gly Thr Phe Thr Ser Asp Leu Ser Lys Gln Leu Glu Ala
 1               5                  10                  15

Glu Ala Val Arg Leu Phe Ile Glu Phe Leu Lys Asn
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 48

Ala Gly Asp Gly Thr Phe Thr Ser Asp Leu Ser Lys Gln Met Glu Glu
 1               5                  10                  15

Ala Ala Val Arg Leu Phe Ile Glu Trp Leu Lys Asn
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 49

Ala Gly Asp Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 50

Ala Gly Asp Gly Thr Phe Thr Ser Asp Leu Ser Lys Gln Met Glu Glu
1               5                   10                  15

Glu Ala Ala Arg Leu Phe Ile Glu Trp Leu Lys Asn
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 51

Ala Gly Asp Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 52

Ala Gly Asp Gly Thr Phe Thr Ser Asp Leu Ser Lys Gln Met Glu Glu
1               5                   10                  15

Glu Ala Val Ala Leu Phe Ile Glu Trp Leu Lys Asn
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 53

Ala Gly Asp Gly Thr Phe Thr Ser Asp Leu Ser Lys Gln Leu Glu Glu
1               5                   10                  15

```
Glu Ala Val Ala Leu Phe Ile Glu Phe Leu Lys Asn
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 54

Ala Gly Asp Gly Thr Phe Thr Ser Asp Leu Ser Lys Gln Met Glu Glu
 1               5                  10                  15

Glu Ala Val Arg Ala Phe Ile Glu Trp Leu Lys Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 55

Ala Gly Asp Gly Thr Phe Thr Ser Asp Leu Ser Lys Gln Leu Glu Glu
 1               5                  10                  15

Glu Ala Val Arg Ala Phe Ile Glu Phe Leu Lys Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (22)
<223> OTHER INFORMATION: naphthylalanine

<400> SEQUENCE: 56

Ala Gly Asp Gly Thr Phe Thr Ser Asp Leu Ser Lys Gln Met Glu Glu
 1               5                  10                  15

Glu Ala Val Arg Leu Xaa Ile Glu Trp Leu Lys Asn
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (22)
<223> OTHER INFORMATION: naphthylalanine
```

<400> SEQUENCE: 57

Ala Gly Asp Gly Thr Phe Thr Ser Asp Leu Ser Lys Gln Leu Glu Glu
1               5                   10                  15

Glu Ala Val Arg Leu Xaa Ile Glu Phe Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 58

Ala Gly Asp Gly Thr Phe Thr Ser Asp Leu Ser Lys Gln Met Glu Glu
1               5                   10                  15

Glu Ala Val Arg Leu Phe Val Glu Trp Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 59

Ala Gly Asp Gly Thr Phe Thr Ser Asp Leu Ser Lys Gln Leu Glu Glu
1               5                   10                  15

Glu Ala Val Arg Leu Phe Val Glu Phe Leu Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (23)
<223> OTHER INFORMATION: tert-butylglycine

<400> SEQUENCE: 60

Ala Gly Asp Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:

<223> OTHER INFORMATION: c-term amidation
<220> FEATURE:
<221> NAME/KEY: MOD_RES
<222> LOCATION: (23)
<223> OTHER INFORMATION: tert-butylglycine

<400> SEQUENCE: 61

Ala Gly Asp Gly Thr Phe Thr Ser Asp Leu Ser Lys Gln Leu Glu Glu
 1               5                  10                  15

Glu Ala Val Arg Leu Phe Xaa Glu Phe Leu Lys Asn
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 62

Ala Gly Asp Gly Thr Phe Thr Ser Asp Leu Ser Lys Gln Met Glu Glu
 1               5                  10                  15

Glu Ala Val Arg Leu Phe Ile Asp Trp Leu Lys Asn
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 63

Ala Gly Asp Gly Thr Phe Thr Ser Asp Leu Ser Lys Gln Leu Glu Glu
 1               5                  10                  15

Glu Ala Val Arg Leu Phe Ile Asp Phe Leu Lys Asn
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 64

Ala Gly Asp Gly Thr Phe Thr Ser Asp Leu Ser Lys Gln Met Glu Glu
 1               5                  10                  15

Glu Ala Val Arg Leu Phe Ile Glu Ala Leu Lys Asn
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Exendin
      agonist

```
<220> FEATURE:
<223> OTHER INFORMATION: c-term amidation

<400> SEQUENCE: 65

Ala Gly Asp Gly Thr Phe Thr Ser Asp Leu Ser Lys Gln Leu Glu Glu
 1               5                  10                  15

Glu Ala Val Arg Leu Phe Ile Glu Ala Leu Lys Asn
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 66

Ala Gly Asp Gly Thr Phe Thr Ser Asp Leu Ser Lys Gln Met Glu Glu
 1               5                  10                  15

Glu Ala Val Arg Leu Phe Ile Glu Trp Ala Lys Asn
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 67

Ala Gly Asp Gly Thr Phe Thr Ser Asp Leu Ser Lys Gln Leu Glu Glu
 1               5                  10                  15

Glu Ala Val Arg Leu Phe Ile Glu Phe Ala Lys Asn
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 68

Ala Gly Asp Gly Thr Phe Thr Ser Asp Leu Ser Lys Gln Met Glu Glu
 1               5                  10                  15

Glu Ala Val Arg Leu Phe Ile Glu Trp Leu Ala Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
```

```
<400> SEQUENCE: 69

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Ala Asn
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 70

Ala Gly Asp Gly Thr Phe Thr Ser Asp Leu Ser Lys Gln Met Glu Glu
 1               5                  10                  15

Glu Ala Val Arg Leu Phe Ile Glu Trp Leu Lys Ala
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 71

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Lys Ala
            20                  25

<210> SEQ ID NO 72
<211> LENGTH: 38
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 72

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro
         35

<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
```

```
<400> SEQUENCE: 73

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 74

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 75
<211> LENGTH: 36
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 75

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 76

Ala Gly Glu Gly Thr Phe Thr Ser Asp Ala Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 77
```

```
<211> LENGTH: 35
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 77

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
         35

<210> SEQ ID NO 78
<211> LENGTH: 34
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 78

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly

<210> SEQ ID NO 79
<211> LENGTH: 35
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 79

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala

<210> SEQ ID NO 80
<211> LENGTH: 33
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 80

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
```

```
                    20                  25                  30

Ser

<210> SEQ ID NO 81
<211> LENGTH: 32
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 81

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 82

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 83

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 84

His Gly Glu Gly Thr Phe Thr Ser Ala Leu Ser Lys Gln Leu Glu Glu
 1               5                  10                  15

Glu Ala Val Arg Leu Phe Ile Glu Phe Leu Lys Asn Gly Gly
            20                  25                  30
```

```
<210> SEQ ID NO 85
<211> LENGTH: 29
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 85

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly
            20                  25

<210> SEQ ID NO 86
<211> LENGTH: 38
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (31)
<223> OTHER INFORMATION: thioproline
<220> FEATURE:
<221> NAME/KEY: MOD_RES
<222> LOCATION: (36)..(38)
<223> OTHER INFORMATION: thioproline

<400> SEQUENCE: 86

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa
        35

<210> SEQ ID NO 87
<211> LENGTH: 38
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (36)..(38)
<223> OTHER INFORMATION: thioproline

<400> SEQUENCE: 87

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 88
<211> LENGTH: 37
```

```
<212> TYPE: PRT
<213> ORGANISM: Artificial Sequence
<220> FEATURE:
<223> OTHER INFORMATION: Description of Artificial Sequence: Ex -continued
<210> SEQ ID NO 91
<211> LENGTH: 30
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation

<400> SEQUENCE: 91

His Gly Asp Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 92
<211> LENGTH: 39
<212> TYPE: PRT
<213> ORGANISM: Artificial Sequence
<220> FEATURE:
<223> OTHER INFORMATION: Description of Artificial Sequence: Exendin
     agonist
<220> FEATURE:
<223> OTHER INFORMATION: c-term amidation

<400> SEQUENCE: 92

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 93
<211> LENGTH: 39
<212> TYPE: PRT
<213> ORGANISM: Artificial Sequence
<220> FEATURE:
<223> OTHER INFORMATION: Description of Artificial Sequence: Exendin
     agonist
<220> FEATURE:
<223> OTHER INFORMATION: c-term amidation

<400> SEQUENCE: 93

Ala Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 94
<211> LENGTH: 41
<212> TYPE: PRT
<213> ORGANISM: Artificial Sequence
<220> FEATURE:
<223> OTHER INFORMATION: Description of Artificial Sequence: Exendin
      agonist
      formula peptide
<220> FEATURE:
<223> OTHER INFORMATION: c-term may be amidated
<220> FEATURE:
<221> NAME/KEY: MOD_RES
<222> LOCATION: (1)
<223> OTHER INFORMATION: His, Arg, Tyr, Ala, Norval, Val, Norleu or
      4-imidazopropionyl -continued

```
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (4)
<223> OTHER INFORMATION: Ala, Norval, Val, Norleu or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Ala, Norval, Val, Norleu, Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)..(22)
<223> OTHER INFORMATION: Ala, Leu, Lys-NH(epsilon)-Lys, or
      Lys-NH(epsilon)-Arg; this range may encompass 1-2 residues
      according to the specification as filed; see specification for
      detailed description of preferred embodiments
```

```
<220> FEATURE:
<221> NAME/KEY: MOD_RES
<222> LOCATION: (23)
<223> OTHER INFORMATION: Phe, Tyr or naphthylalanine
<220> FEATURE:
<221> NAME/KEY: MOD_RES
<222> LOCATION: (24)
<223> OTHER INFORMATION: Ile, Val, Leu, pentylglycine, tert-butylglycine
     or Met
<220> FEATURE:
<221> NAME/KEY: MOD_RES
<222> LOCATION: (25)
<223> OTHER INFORMATION: Ala, Glu or Asp
<220> FEATURE:
<221> NAME/KEY: MOD_RES
<222> LOCATION: (26)
<223> OTHER INFORMATION: Ala, Trp, Phe, Tyr or naphthylalanine
<220> FEATURE:
<221> NAME/KEY: MOD_RES
<222> LOCATION: (27)
<223> OTHER INFORMATION: Ala or Leu
<220> FEATURE:
<221> NAME/KEY: MOD_RES
<222> LOCATION: (28)..(30)
<223> OTHER INFORMATION: Lys-Asn, Asn-Lys, Lys-NH(epsilon)-Lys-Asn,
     Lys-NH(epsilon)-Arg-Asn, Asn-Lys-NH(epsilon)-Lys,
     Asn-Lys-NH(epsilon)-Arg, Lys-NH(epsilon)-Lys-Ala,
     Lys-NH(epsilon)-Arg-Ala, Ala-Lys-NH(epsilon)-Lys, or
     Ala-Lys-NH(epsilon)-Arg
<220> FEATURE:
<223> OTHER INFORMATION: this range may encompass 2-3 residues according
     to the specification as filed; see specification for
     detailed description of preferred embodiments
<220> FEATURE:
<221> NAME/KEY: MOD_RES
<222> LOCATION: (33)
<223> OTHER INFORMATION: Pro, homoproline, 3Hyp, 4Hyp, thioproline,
     N-alkylglycine, N-alkylpentlyglycine and N-alkylalanine
<220> FEATURE:
<221> NAME/KEY: MOD_RES
<222> LOCATION: (38)..(40)
<223> OTHER INFORMATION: Pro, homoproline, 3Hyp, 4Hyp, thioproline,
     N-alkylglycine, N-alkylpentlyglycine and N-alkylalanine
<220> FEATURE:
<221> NAME/KEY: MOD_RES
<222> LOCATION: (41)
<223> OTHER INFORMATION: Ser or Tyr
<220> FEATURE:
<223> OTHER INFORMATION: provided that no more than three of Xaa3, Xaa4,
     Xaa5, Xaa6, Xaa8, Xaa9, Xaa10, Xaa11, Xaa12, Xaa13, Xaa14, Xaa15,
     Xaa16, Xaa17, Xaa19, Xaa20, Xaa21, Xaa24, Xaa25, Xaa26
     are Ala
<220> FEATURE:
<223> OTHER INFORMATION: provided also that, if Xaa1 is His, Arg, Tyr or
     4-imidazopropionyl then at least one of Xaa3, Xaa4 and
     Xaa9 is Ala
<220> FEATURE:
<223> OTHER INFORMATION: this peptide may encompass 28-41 residues,
     wherein residues 1-20 are constant and residues 21-41 may vary in
     length according to the specification as filed; see specification
     for detailed description of substitutions and preferred
     embodiments

<400> SEQUENCE: 94

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Gly Gly
             20                  25                  30

Xaa Ser Ser Gly Ala Xaa Xaa Xaa Xaa
         35                  40

<210> SEQ ID NO 95
<211> LENGTH: 27
<212> TYPE: PRT
<213> ORGANISM: Artificial Sequence
```

```
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH(epsilon)octanoyl

<400> SEQUENCE: 95

Xaa Glu Gly Thr Phe Thr Ser Ala Leu Ser Lys Gln Met Glu Glu Glu
 1               5                  10                  15

Ala Val Arg Leu Phe Ile Glu Trp Leu Xaa Asn
             20                  25

<210> SEQ ID NO 96
<211> LENGTH: 27
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH(epsilon)octanoyl

<400> SEQUENCE: 96

Xaa Glu Gly Thr Phe Thr Ser Ala Leu Ser Lys Gln Leu Glu Glu Glu
 1               5                  10                  15

Ala Val Arg Leu Phe Ile Glu Phe Leu Xaa Asn
             20                  25

<210> SEQ ID NO 97
<211> LENGTH: 29
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH(epsilon)octanoyl

<400> SEQUENCE: 97

Xaa Glu Gly Thr Phe Thr Ser Ala Leu Ser Lys Gln Met Glu Glu Glu
 1               5                  10                  15

Ala Val Arg Leu Phe Ile Glu Trp Leu Xaa Asn Gly Gly
             20                  25

<210> SEQ ID NO 98
<211> LENGTH: 29
```

```
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (26)
<223> OTHER INFORMATION: Lys-NH(epsilon)octanoyl

<400> SEQUENCE: 98

Xaa Glu Gly Thr Phe Thr Ser Ala Leu Ser Lys Gln Leu Glu Glu
 1               5                  10                  15

Ala Val Arg Leu Phe Ile Glu Phe Leu Xaa Asn Gly Gly
            20                  25

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH(epsilon)octanoyl

<400> SEQUENCE: 99

Xaa Glu Gly Thr Phe Thr Ser Ala Leu Ser Lys Gln Met Glu Glu Glu
 1               5                  10                  15

Ala Val Arg Leu Phe Ile Glu Trp Leu Asn Xaa
            20                  25

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH(epsilon)octanoyl

<400> SEQUENCE: 100

Xaa Glu Gly Thr Phe Thr Ser Ala Leu Ser Lys Gln Leu Glu Glu Glu
 1               5                  10                  15

Ala Val Arg Leu Phe Ile Glu Phe Leu Asn Xaa
            20                  25
```

```
<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH(epsilon)octanoyl

<400> SEQUENCE: 101

Xaa Glu Gly Thr Phe Thr Ser Ala Leu Ser Lys Gln Met Glu Glu
 1               5                  10                  15

Ala Val Arg Leu Phe Ile Glu Trp Leu Asn Xaa Gly Gly
            20                  25

<210> SEQ ID NO 102
<211> LENGTH: 29
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (1)
<223> OTHER INFORMATION: 4-imidazolylpropionyl-Gly
<220> FEATURE:
<221> NAME/KEY: MOD_RES
<222> LOCATION: (27)
<223> OTHER INFORMATION: Lys-NH(epsilon)octanoyl

<400> SEQUENCE: 102

Xaa Glu Gly Thr Phe Thr Ser Ala Leu Ser Lys Gln Leu Glu Glu
 1               5                  10                  15

Ala Val Arg Leu Phe Ile Glu Phe Leu Asn Xaa Gly Gly
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 103

Ala Gly Glu Gly Thr Phe Thr Ser Asp Leu Ser Lys Gln Met Glu
 1               5                  10                  15

Glu Ala Val Arg Leu Phe Ile Glu Trp Leu Xaa Asn
            20                  25

<210> SEQ ID NO 104
<211> LENGTH: 28
```

```
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 104

Ala Gly Glu Gly Thr Phe Thr Ser Asp Leu Ser Lys Gln Leu Glu Glu
  1               5                  10                  15

Glu Ala Val Arg Leu Phe Ile Glu Phe Leu Xaa Asn
             20                  25

<210> SEQ ID NO 105
<211> LENGTH: 30
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 105

Ala Gly Glu Gly Thr Phe Thr Ser Asp Leu Ser Lys Gln Met Glu Glu
  1               5                  10                  15

Glu Ala Val Arg Leu Phe Ile Glu Trp Leu Xaa Asn Gly Gly
             20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 106

Ala Gly Glu Gly Thr Phe Thr Ser Asp Leu Ser Lys Gln Leu Glu Glu
  1               5                  10                  15

Glu Ala Val Arg Leu Phe Ile Glu Phe Leu Xaa Asn Gly Gly
             20                  25                  30

<210> SEQ ID NO 107
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
```

```
<223> OTHER INFORMATION: Lys-NH(epsilon)octanoyl

<400> SEQUENCE: 107

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Asn Xaa
            20                  25

<210> SEQ ID NO 108
<211> LENGTH: 28
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 108

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa
            20                  25

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 109

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Asn Xaa Gly Gly
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Exendin
      agonist
<220> FEATURE:
<223> OTHER INFORMATION: c-term amidation
<220> FEATURE:
<221> NAME/KEY: MOD_RES
<222> LOCATION: (27)
<223> OTHER INFORMATION: Lys-NH(epsilon)octanoyl

<400> SEQUENCE: 110

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa Gly Gly
            20                  25                  30
```

EXENDIN AGONIST PEPTIDES

RELATED APPLICATION

This application claims the benefit of U.S. Provisional Application No. 60/066,029, filed Nov. 14, 1997, the contents of which are hereby incorporated by reference in their entirety.

FIELD OF THE INVENTION

The present invention relates to novel compounds which have activity as exendin agonists. These compounds are useful in treatment of Type I and II diabetes, in treatment of disorders which would be benefited by agents which lower plasma glucose levels and in treatment of disorders which would be benefited with agents useful in delaying and/or slowing gastric emptying.

BACKGROUND

The following description includes information that may be useful in understanding the present invention. It is not an admission that any of the information provided herein is prior art to the presently claimed invention, nor that any of the publications specifically or implicitly referenced are prior art to that invention.

Exendin

The exendins are peptides that are found in the venom of the Gila-monster, a lizard endogenous to Arizona and Northern Mexico. Exendin-3 [SEQ. ID. NO. 1] is present in the venom of *Heloderma horridum*, and exendin-4 [SEQ. ID. NO. 2] is present in the venom of *Heloderma suspectum* (Eng, J., et al., *J. Biol. Chem.*, 265:20259–62, 1990; Eng., J., et al., *J. Biol. Chem.*, 267:7402–05, 1992). The amino acid sequence of exendin-3 is shown in FIG. 1. The amino acid sequence of exendin-4 is shown in FIG. 2. The exendins have some sequence similarity to several members of the glucagon-like peptide family, with the highest homology, 53%, being to GLP-1[7–36]NH$_2$ [SEQ. ID. NO. 3] (Goke, et al., *J. Biol. Chem.*, 268:19650–55, 1993). GLP-1[7–36]NH$_2$, also known as proglucagon[78–107] or simply "GLP-1" as used most often herein, has an insulinotropic effect, stimulating insulin secretion from pancreatic β-cells; GLP-1 also inhibits glucagon secretion from pancreatic α-cells (Ørsov, et al., *Diabetes*, 42:658–61, 1993; D'Alessio, et al., *J. Clin. Invest.*, 97:133–38, 1996). The amino acid sequence of GLP-1 is shown in FIG. 3. GLP-1 is reported to inhibit gastric emptying (Willms B, et al., *J Clin Endocrinol Metab* 81 (1): 327–32, 1996; Wettergren A, et al., *Dig Dis Sci* 38 (4): 665–73, 1993), and gastric acid secretion. Schjoldager B T, et al., *Dig Dis Sci* 34 (5): 703–8, 1989; O'Halloran D J, et al., *J Endocrinol* 126 (1): 169–73, 1990; Wettergren A, et al., *Dig Dis Sci* 38 (4): 665–73, 1993). GLP-1[7–37], which has an additional glycine residue at its carboxy terminus, also stimulates insulin secretion in humans (Ørsov, et al., *Diabetes*, 42:658–61, 1993). A transmembrane G-protein adenylate-cyclase-coupled receptor believed to be responsible for the insulinotropic effect of GLP-1 has been cloned from a β-cell line (Thorens, *Proc. Natl. Acad. Sci. USA* 89:8641–45, 1992), hereinafter referred to as the "cloned GLP-1 receptor." Exendin-4 reportedly acts at GLP-1 receptors on insulin-secreting βTC1 cells, at dispersed acinar cells from guinea pig pancreas, and at parietal cells from stomach; the peptide is also reported to stimulate somatostatin release and inhibit gastrin release in isolated stomachs (Goke, et al., *J. Biol. Chem.* 268:19650–55, 1993; Schepp, et al., *Eur. J. Pharmacol.*, 69:183–91, 1994; Eissele, et al., *Life Sci.*, 55:629–34, 1994). Exendin-3 and exendin-4 were reportedly found to stimulate cAMP production in, and amylase release from, pancreatic acinar cells (Malhotra, R., et al., *Regulatory Peptides*, 41:149–56, 1992; Raufman, et al., *J. Biol. Chem.* 267:21432–37, 1992; Singh, et al., *Regul. Pept.* 53:47–59, 1994). Based on their insulinotropic activities, the use of exendin-3 and exendin-4 for the treatment of diabetes mellitus and the prevention of hyperglycemia has been proposed (Eng, U.S. Pat. No. 5,424,286).

Agents which serve to delay gastric emptying have found a place in medicine as diagnostic aids in gastro-intestinal radiologic examinations. For example, glucagon is a polypeptide hormone which is produced by the α cells of the pancreatic islets of Langerhans. It is a hyperglycemic agent which mobilizes glucose by activating hepatic glycogenolysis. It can to a lesser extent stimulate the secretion of pancreatic insulin. Glucagon is used in the treatment of insulin-induced hypoglycemia, for example, when administration of glucose intravenously is not possible. However, as glucagon reduces the motility of the gastro-intestinal tract it is also used as a diagnostic aid in gastro-intestinal radiological examinations. Glucagon has also been used in several studies to treat various painful gastro-intestinal disorders associated with spasm. Daniel, et al. (Br. Med. J., 3:720; 1974) reported quicker symptomatic relief of acute diverticulitis in patients treated with glucagon compared with those who had been treated with analgesics or antispasmodics. A review by Glauser, et al. (*J. Am. Coll. Emergency Physns*, 8:228, 1979) described relief of acute esophageal food obstruction following glucagon therapy. In another study, glucagon significantly relieved pain and tenderness in 21 patients with biliary tract disease compared with 22 patients treated with placebo (M. J. Stower, et al., *Br. J. Surg.*, 69:591–2, 1982).

Methods for regulating gastrointestinal motility using amylin agonists are described in International Application No. PCT/US94/10225, published Mar. 16, 1995.

Methods for regulating gastrointestinal motility using exendin agonists are described in U.S. patent application Ser. No. 08/908,867, filed Aug. 8, 1997 entitled "Methods for Regulating Gastrointestinal Motility," which application is a continuation-in-part of U.S. patent application Ser. No. 08/694,954 filed Aug. 8, 1996.

Methods for reducing food intake using exendin agonists are described in U.S. patent application Ser. No. 09/003,869, filed Jan. 7, 1998, entitled "Use of Exendin and Agonists Thereof for the Reduction of Food Intake," which claims the benefit of U.S. Provisional Application Nos. 60/034,905 filed Jan. 7, 1997, 60/055,404 filed Aug. 7, 1997, 60/065,442 filed Nov. 14, 1997 and 60/066,029 filed Nov. 14, 1997.

Novel exendin agonist compounds are described in PCT Application Serial No. PCT/US98/16387 filed Aug. 6, 1998, entitled "Novel Exendin Agonist Compounds," which claims the benefit of U.S. Patent Application Ser. No. 60/055,404, filed Aug. 8, 1997. Other novel exendin agonists are described in U.S. application Ser. No. 09/554,533 filed Nov. 13, 1998, entitled "Novel Exendin Agonist Compounds," which claims the benefit of U.S. Provisional Application No. 60/065,442 filed Nov. 14, 1997.

SUMMARY OF THE INVENTION

According to one aspect, the present invention provides novel exendin agonist compounds which exhibit advantageous properties which include effects in slowing gastric emptying and lowering plasma glucose levels.

According to the present invention, provided are compounds of the formula (I) [SEQ. ID. NO. 4]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

$Xaa_1$ is His, Arg, Tyr, Ala, Norval, Val or Norleu;

$Xaa_2$ is Ser, Gly, Ala or Thr;

$Xaa_3$ is Ala, Asp or Glu;

$Xaa_4$ is Ala, Norval, Val, Norleu or Gly;

$Xaa_5$ is Ala or Thr;

$Xaa_6$ is Phe, Tyr or naphthylalanine;

$Xaa_7$ is Thr or Ser;

$Xaa_8$ is Ala, Ser or Thr;

$Xaa_9$ is Ala, Norval, Val, Norleu, Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is

—OH,

—$NH_2$,

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$,

Gly Gly $Xaa_{31}$ Ser Ser Gly Ala $Xaa_{36}$ $Xaa_{37}$ $Xaa_{38}$-$Z_2$ or

Gly Gly $Xaa_{31}$ Ser Ser Gly Ala $Xaa_{36}$ $Xaa_{37}$ $Xaa_{38}$ Ser-$Z_2$;

wherein $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is —OH or —$NH_2$;

provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

Also included within the scope of the present invention are pharmaceutically acceptable salts of the compounds of formula (I) and pharmaceutical compositions including said compounds and salts thereof.

Also within the scope of the present invention are narrower genera of peptide compounds of various lengths, for example, genera of compounds which do not include peptides having a length of 28, 29 or 30 amino acid residues, respectively.

Additionally, the present invention includes narrower genera of peptide compounds having particular amino acid sequences, for example, compounds of formula [I][SEQ. ID. NO. 4]:

```
Xaa1  Xaa2  Xaa3  Xaa4  Xaa5  Xaa6  Xaa7  Xaa8  Xaa9  Xaa10

Xaa11 Xaa12 Xaa13 Xaa14 Xaa15 Xaa16 Xaa17 Ala   Xaa19

Xaa20 Xaa21 Xaa22 Xaa23 Xaa24 Xaa25 Xaa26 Xaa27

Xaa28-Z1;
```

$Xaa_1$ is His or Ala;

$Xaa_2$ is Gly or Ala;

$Xaa_3$ is Ala, Asp or Glu;

$Xaa_4$ is Ala or Gly;

$Xaa_5$ is Ala or Thr;

$Xaa_6$ is Phe or naphthylalanine;

$Xaa_7$ is Thr or Ser;

$Xaa_8$ is Ala, Ser or Thr;

$Xaa_9$ is Ala, Asp or Glu;

$Xaa_{10}$ is Ala, Leu or pentylglycine;

$Xaa_{11}$ is Ala or Ser;

$Xaa_{12}$ is Ala or Lys;

$Xaa_{13}$ is Ala or Gln;

$Xaa_{14}$ is Ala, Leu, Met or pentylglycine;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala or Leu;

$Xaa_{22}$ is Phe or naphthylalanine;

$Xaa_{23}$ is Ile, Val or tert-butylglycine;

$Xaa_{24}$ is Ala, Glu or Asp;

$Xaa_{25}$ is Ala, Trp or Phe;

$Xaa_{26}$ is Ala or Leu;

$Xaa_{27}$ is Ala or Lys;

$Xaa_{28}$ is Ala or Asn;

$Z_1$ is

```
-OH,
-NH2,
Gly-Z2,
Gly Gly-Z2
Gly Gly Xaa31-Z2,
Gly Gly Xaa31 Ser-Z2,
Gly Gly Xaa31 Ser Ser-Z2,
Gly Gly Xaa31 Ser Ser Gly-Z2,
Gly Gly Xaa31 Ser Ser Gly Ala-Z2,
Gly Gly Xaa31 Ser Ser Gly Ala Xaa36-Z2,
Gly Gly Xaa31 Ser Ser Gly Ala Xaa36 Xaa37-Z2
Gly Gly Xaa31 Ser Ser Gly Ala Xaa36 Xaa37 Xaa38-Z2
Gly Gly Xaa31 Ser Ser Gly Ala Xaa36 Xaa37 Xaa38 Ser-Z2;
```

$Xaa_{31}$, $Xaa_{36}$, $Xaa_{37}$ and $Xaa_{38}$ are independently Pro, homoproline, thioproline, or N-methylalanine; and $Z_2$ is —OH or —NH$_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and provided that, if $Xaa_1$ is His, Arg or Tyr, then at least one of $Xaa_3$, $Xaa_4$ and $Xaa_9$ is Ala; and pharmaceutically acceptable salts thereof.

Also provided are peptide compounds of the formula (II) [SEQ. ID. NO. 94]:

```
                  5
Xaa1 Xaa2 Xaa3 Xaa4 Xaa5 Xaa6 Xaa7 Xaa8 Xaa9
10
Xaa10 Xaa11 Xaa12 Xaa13 Xaa14 Xaa15 Xaa16 Xaa17 Ala
Xaa19 Xaa20 Xaa21 Xaa22 Xaa23 Xaa24 Xaa25 Xaa26 X1-Z1;

Xaa11 Xaa12 Xaa13 Xaa14 Xaa15 Xaa16 Xaa17 Ala Xaa19
  Xaa20 Xaa21 Xaa22 Xaa23 Xaa24 Xaa25 Xaa26 X1-Z1;
wherein
```

$Xaa_1$ is His, Arg, Tyr, Ala, Norval, Val, Norleu or 4-imidazopropionyl;

$Xaa_2$ is Ser, Gly, Ala or Thr;

$Xaa_3$ is Ala, Asp or Glu;

$Xaa_4$ is Ala, Norval, Val, Norleu or Gly;

$Xaa_5$ is Ala or Thr;

$Xaa_6$ is Phe, Tyr or naphthylalanine;

$Xaa_7$ is Thr or Ser;

$Xaa_8$ is Ala, Ser or Thr;

$Xaa_9$ is Ala, Norval, Val, Norleu, Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala, Leu or Lys-NH$^\epsilon$-R where R is Lys, Arg, $C_1$–$C_{10}$ straight chain or branched alkanoyl or cycloalleyl-alkanoyl;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$X_1$ is Lys Asn, Asn Lys, Lys-NH$^\epsilon$-R Asn, Asn Lys-NH$^\epsilon$-R, Lys-NH$^\epsilon$-R Ala, Ala Lys-NH$^\epsilon$-R where R is Lys, Arg, $C_1$–$C_{10}$ straight chain or branched alkanoyl or cycloalkylalkanoyl $Z_1$ is

—OH,

—NH$_2$,

Gly-$Z_2$,

Gly Gly-$Z_2$,

Gly Gly Xaa$_{31}$-$Z_2$,

Gly Gly Xaa$_{31}$ Ser-$Z_2$,

Gly Gly Xaa$_{31}$ Ser Ser-$Z_2$,

Gly Gly Xaa$_{31}$ Ser Ser Gly-$Z_2$,

Gly Gly Xaa$_{31}$ Ser Ser Gly Ala-$Z_2$,

Gly Gly Xaa$_{31}$ Ser Ser Gly Ala Xaa$_{36}$-$Z_2$,

Gly Gly Xaa$_{31}$ Ser Ser Gly Ala Xaa$_{36}$ Xaa$_{37}$-$Z_2$,

Gly Gly Xaa$_{31}$ Ser Ser Gly Ala Xaa$_{36}$ Xaa$_{37}$ Xaa$_{38}$-$Z_2$ or

Gly Gly Xaa$_{31}$ Ser Ser Gly Ala Xaa$_{36}$ Xaa$_{37}$ Xaa$_{38}$ Ser-$Z_2$;

wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; and $Z_2$ is —OH or —NH$_2$;

provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, are Ala; and provided also that, if $Xaa_1$ is His, Arg, Tyr, or 4-imidazopropionyl then at least one of $Xaa_3$, $Xaa_4$ and $Xaa_9$ is Ala.

Also within the scope of the present invention are pharmaceutically acceptable salts of the compounds of formula (II) and pharmaceutical compositions including said compounds and salts thereof.

Preferred compounds of formula (II) include those wherein $Xaa_1$ is His, Ala, Norval or 4-imidazopropionyl. Preferably, $Xaa_1$ is His, or 4-imidazopropionyl or Ala, more preferably His or 4-imidazopropionyl.

Preferred compounds of formula (II) include those wherein $Xaa_2$ is Gly.

Preferred compounds of formula (II) include those wherein $Xaa_4$ is Ala.

Preferred compounds of formula (II) include those wherein $Xaa_9$ is Ala.

Preferred compounds of formula (II) include those wherein $Xaa_{14}$ is Leu, pentylglycine or Met.

Preferred compounds of formula (II) include those wherein $Xaa_{25}$ is Trp or Phe.

Preferred compounds of formula (II) include those wherein $Xaa_6$ is Ala, Phe or naphthylalanine; $Xaa_{22}$ is Phe or naphthylalanine; and $Xaa_{23}$ is Ile or Val.

Preferred compounds of formula (II) include those wherein $Z_1$ is —NH$_2$.

Preferred compounds of formula (II) include those wherein $Xaa_{31}$, $Xaa_{36}$, $Xaa_{37}$ and $Xaa_{38}$ are independently selected from the group consisting of Pro, homoproline, thioproline and N-alkylalanine.

Preferred compounds of formula (II) include those wherein $Xaa_{39}$ is Ser or Tyr, preferably Ser.

Preferred compounds of formula (II) include those wherein $Z_2$ is —NH$_2$.

Preferred compounds of formula (II) include those wherein $Z_1$ is —NH$_2$.

Preferred compounds of formula (II) include those wherein Xaa$_{21}$ is Lys-NH$^\epsilon$-R where R is Lys, Arg, C$_1$–C$_{10}$ straight chain or branched alkanoyl.

Preferred compounds of formula (II) include those wherein X$_1$ is Lys Asn, Lys-NH$^\epsilon$-R Asn, or Lys-NH$^\epsilon$-R Ala where R is Lys, Arg, C$_1$–C$_{10}$ straight chain or branched alkanoyl.

Preferred compounds of formula (II) include those having an amino acid sequence selected from SEQ. ID. NOS. 95–110.

Definitions

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or (2)

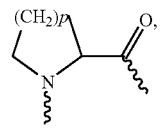

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following:

"ACN" or "CH$_3$CN" refers to acetonitrile.

"Boc", "tBoc" or "Tboc" refers to t-butoxy carbonyl.

"DCC" refers to N,N'-dicyclohexylcarbodiimide.

"Fmoc" refers to fluorenylmethoxycarbonyl.

"HBTU" refers to 2-(1H-benzotriazol-1-yl)-1,1,3,3,-tetramethyluronium hexaflurophosphate.

"HOBt" refers to 1-hydroxybenzotriazole monohydrate.

"homoP" or hpro" refers to homoproline.

"MeAla" or "Nme" refers to N-methylalanine.

"naph" refers to naphthylalanine.

"pG" or "pGly" refers to pentylglycine.

"tBuG" refers to tertiary-butylglycine.

"ThioP" or tPro" refers to thioproline.

"3Hyp" refers to 3-hydroxyproline

"4Hyp" refers to 4-hydroxyproline

"NAG" refers to N-alkylglycine

"NAPG" refers to N-alkylpentylglycine

"Norval" refers to norvaline

"Norleu" refers to norleucine

BRIEF DESCRIPTION OF THE DRAWINGS

FIG. 1 depicts the amino acid sequence for exendin-3 [SEQ. ID. NO. 1].

FIG. 2 depicts the amino acid sequence for exendin-4 [SEQ. ID. NO. 2].

FIG. 3 depicts the amino acid sequence for GLP-1[7–36] NH$_2$ (GLP-1) [SEQ. ID. NO. 3].

FIG. 4 depicts the amino acid sequences for certain compounds of the present invention, Compounds 1–89 [SEQ. ID. NOS. 5 to 93].

FIG. 7 depicts the amino acid sequences for certain compounds of the present invention, Compound Nos. 90–105 [SEQ. ID. NOS. 95–110].

DETAILED DESCRIPTION OF THE INVENTION

Figure 5:
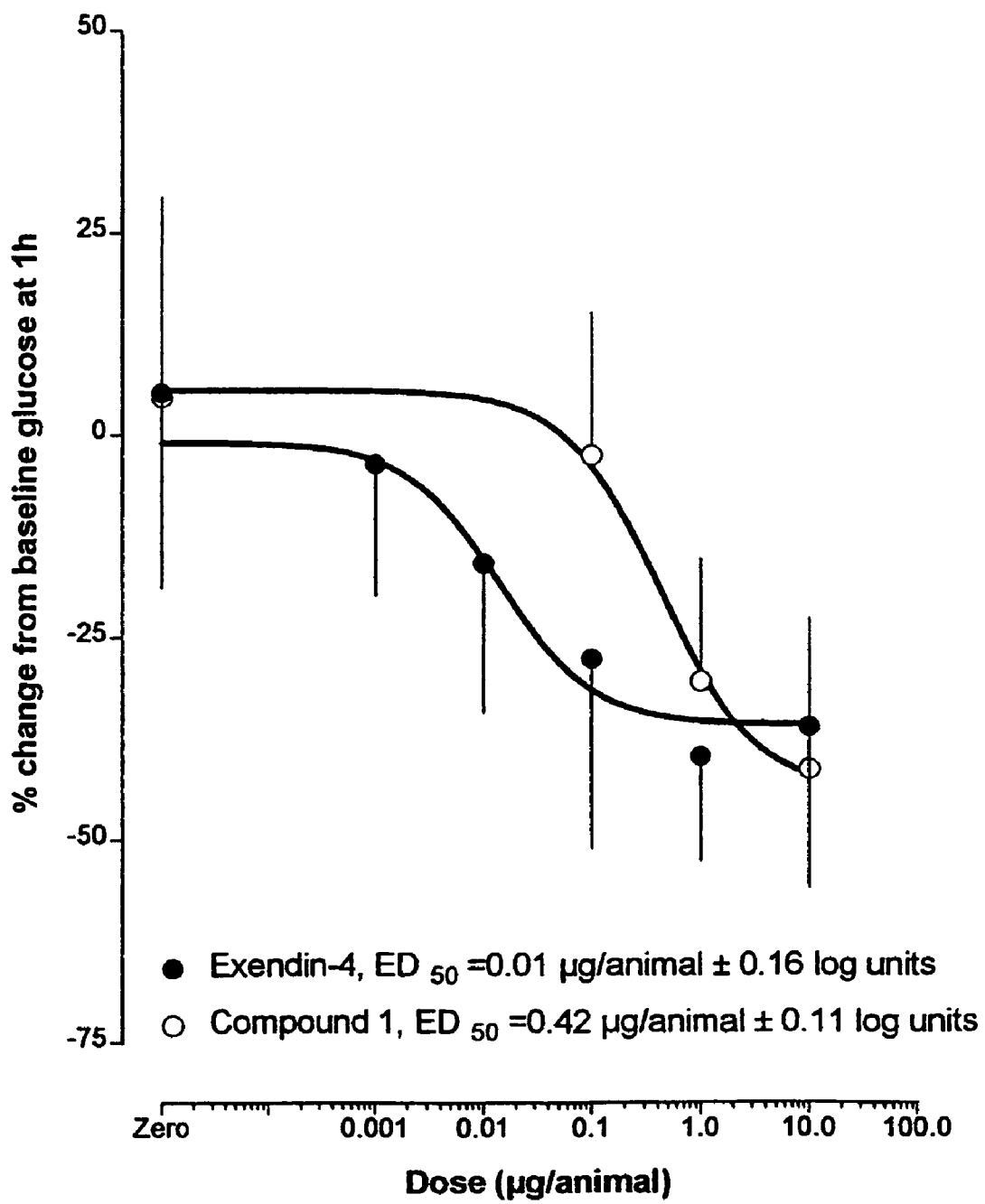
FIG. 5 depicts the effect on lowering blood glucose of various concentrations of Compound 1 [SEQ. ID. NO. 5].

According to the present invention, provided are compounds of the formula (I) [SEQ. ID. NO. 4]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$; wherein $Xaa_1$ is His, Arg, Tyr, Ala, Norval, Val or Norleu;

$Xaa_2$ is Ser, Gly, Ala or Thr;

$Xaa_3$ is Ala, Asp or Glu;

$Xaa_4$ is Ala, Norval, Val, Norleu or Gly;

$Xaa_5$ is Ala or Thr;

$Xaa_6$ is Phe, Tyr or naphthylalanine;

$Xaa_7$ is Thr or Ser;

$Xaa_8$ is Ala, Ser or Thr;

$Xaa_9$ is Ala, Norval, Val, Norleu, Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala, Leu or Lys-$NH^\epsilon R$ where R is Lys, Arg, $C_1$–$C_{10}$ straight chain or branched alkanoyl or cycloalleyl-alkanoyl;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Ala or Lys;

$Xaa_{28}$ is Ala or Asn;

$Z_1$ is

—OH,

—$NH_2$,

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$,

Gly Gly $Xaa_{31}$ Ser Ser Gly Ala $Xaa_{36}$ $Xaa_{37}$ $Xaa_{38}$-$Z_2$ or

Gly Gly $Xaa_{31}$ Ser Ser Gly Ala $Xaa_{36}$ $Xaa_{37}$ $Xaa_{38}$ $Xaa_{39}$-$Z_2$;

wherein $Xaa_{31}$, $Xaa_{36}$, $Xaa_{37}$ and $Xaa_{38}$ are independently selected from Pro, homoproline, 3Hyp, 4Hyp, thioproline, N-alkylglycine, N-alkylpentylglycine or N-alkylalanine; and $Z_2$ is —OH or —$NH_2$;

provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_2$, are Ala; and provided also that, if $Xaa_1$ is His, Arg or Tyr, then at least one of $Xaa_3$, $Xaa_4$ and $Xaa_9$ is Ala. Also within the scope of the present invention are pharmaceutically acceptable salts of formula (I) and pharmaceutic compositions including said compounds and salts thereof.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (I) include those identified in Examples 1–89 ("Compounds 1–89," respectively) [SEQ. ID. NOS. 5 to 93], as well as those corresponding compounds identified in Examples 104 and 105.

Preferred such exendin agonist compounds include those wherein $Xaa_1$ is His, Ala or Norval. More preferably $Xaa_1$ is His or Ala. Most preferably $Xaa_1$ is His.

Preferred are those compounds of formula (I) wherein $Xaa_2$ is Gly.

Preferred are those compounds of formula (I) wherein $Xaa_3$ is Ala.

Preferred are those compounds of formula (I) wherein Xaa$_4$ is Ala.

Preferred are those compounds of formula (I) wherein Xaa$_9$ is Ala.

Preferred are those compounds of formula (I) wherein Xaa$_{14}$ is Leu, pentylglycine or Met.

Preferred compounds of formula (I) are those wherein Xaa$_{25}$ is Trp or Phe.

Preferred compounds of formula (I) are those where Xaa$_6$ is Ala, Phe or naphthylalanine; Xaa$_{22}$ is Phe or naphthylalanine; and Xaa$_{23}$ is Ile or Val.

Preferred are compounds of formula (I) wherein Xaa$_{31}$, Xaa$_{36}$, Xaa$_{37}$ and Xaa$_{38}$ are independently selected from Pro, homoproline, thioproline and N-alkylalanine.

Preferably Z$_1$ is —NH$_2$.
Preferably Z$_2$ is —NH$_2$.

According to one aspect, preferred are compounds of formula (I) wherein Xaa$_1$ is Ala, His or Tyr, more preferably Ala or His; Xaa$_2$ is Ala or Gly; Xaa$_6$ is Phe or naphthylalanine; Xaa$_{14}$ is Ala, Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine; and Xaa$_{39}$ is Ser or Tyr, more preferably Ser. More preferably Z$_1$ is —NH$_2$.

According to an especially preferred aspect, especially preferred compounds include those of formula (I) wherein: Xaa$_1$ is His or Ala; Xaa$_2$ is Gly or Ala; Xaa$_3$ is Ala, Asp or Glu; Xaa$_4$ is Ala or Gly; Xaa$_5$ is Ala or Thr; Xaa$_6$ is Phe or naphthylalanine; Xaa$_7$ is Thr or Ser; Xaa$_8$ is Ala, Ser or Thr; Xaa$_9$ is Ala, Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu, Met or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is Ile, Val or tert-butylglycine; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$, Gly Gly Xaa$_{31}$ Ser Ser Gly Ala Xaa$_{36}$ Xaa$_{37}$ Xaa$_{38}$-Z$_2$ or Gly Gly Xaa$_{31}$ Ser Ser Gly Ala Xaa$_{36}$ Xaa$_{37}$ Xaa$_{38}$ Xaa$_{39}$-Z$_2$; Xaa$_{31}$, Xaa$_{36}$, Xaa$_{37}$ and Xaa$_{38}$ being independently Pro homoproline, thioproline or N-methylalanine; and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$ Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and provided also that, if Xaa$_1$ is His, Arg or Tyr, then at least one of Xaa$_{31}$ Xaa$_4$ and Xaa$_9$ is Ala. Especially preferred compounds of formula (I) include those having the amino acid sequence of SEQ. ID. NOS. 5–93

According to an especially preferred aspect, provided are compounds of formula (I) where Xaa$_{14}$ is Ala, Leu, Ile, Val or pentylglycine, more preferably Leu or pentylglycine, and Xaa$_{25}$ is Ala, Phe, Tyr or naphthylalanine, more preferably Phe or naphthylalanine. These compounds will be less susceptible to oxidative degration, both in vitro and in vivo, as well as during synthesis of the compound.

Also within the scope of the present invention are narrower genera of peptide compounds of various lengths, for example, genera of compounds which do not include peptides having a length of 28, 29 or 30 amino acid residues, respectively.

Additionally, the present invention includes narrower genera of peptide compounds having particular amino acid sequences, for example, compounds of formula [I][SEQ. ID. NO. 4]:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$

Xaa$_{20}$ Xaa$_{21}$ Xaa$_{22}$ Xaa$_{23}$ Xaa$_{24}$ Xaa$_{25}$ Xaa$_{26}$ Xaa$_{27}$

Xaa$_{28}$-Z$_1$;

Xaa$_1$ is His or Ala;

Xaa$_2$ is Gly or Ala;

Xaa$_3$ is Ala, Asp or Glu;

Xaa$_4$ is Ala or Gly;

Xaa$_5$ is Ala or Thr;

Xaa$_6$ is Phe or naphthylalanine;

Xaa$_7$ is Thr or Ser;

Xaa$_8$ is Ala, Ser or Thr;

Xaa$_9$ is Ala, Asp or Glu;

Xaa$_{10}$ is Ala, Leu or pentylglycine;

Xaa$_{11}$ is Ala or Ser;

Xaa$_{12}$ is Ala or Lys;

Xaa$_{13}$ is Ala or Gln;

Xaa$_{14}$ is Ala, Leu, Met or pentylglycine;

Xaa$_{15}$ is Ala or Glu;

Xaa$_{16}$ is Ala or Glu;

Xaa$_{17}$ is Ala or Glu;

Xaa$_{19}$ is Ala or Val;

Xaa$_{20}$ is Ala or Arg;

Xaa$_{21}$ is Ala or Leu;

Xaa$_{22}$ is Phe or naphthylalanine;

Xaa$_{23}$ is Ile, Val or tert-butylglycine;

Xaa$_{24}$ is Ala, Glu or Asp;

Xaa$_{25}$ is Ala, Trp or Phe;

Xaa$_{26}$ is Ala or Leu;

Xaa$_{27}$ is Ala or Lys;

Xaa$_{28}$ is Ala or Asn;

Z$_1$ is

—OH,

—NH$_2$,

Gly-Z$_2$,

Gly Gly-Z$_2$,

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$

Gly Gly Xaa$_{31}$ Ser Ser Gly Ala Xaa$_{36}$ Xaa$_{37}$ Xaa$_{38}$-Z$_2$

Gly Gly Xaa$_{31}$ Ser Ser Gly Ala Xaa$_{36}$ Xaa$_{37}$ Xaa$_{38}$ Ser-Z$_2$;

Xaa$_{31}$, Xaa$_{36}$, Xaa$_{37}$ and Xaa$_{38}$ are independently Pro, homoproline, thioproline, or
N-methylylalanine; and Z$_2$ is —OH or —NH$_2$;

provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$, and Xaa$_{28}$ are Ala; and provided that, if Xaa$_1$ is His, Arg or Tyr, then at least one of Xaa$_3$, Xaa$_4$ and Xaa$_9$ is Ala; and pharmaceutically acceptable salts thereof.

Also provided are peptide compounds of the formula (II) [SEQ. ID. NO. 94]:

5
Xaa$_1$ Xaa$_2$ Xaa$_3$ Xaa$_4$ Xaa$_5$ Xaa$_6$ Xaa$_7$ Xaa$_8$ Xaa$_9$

10
Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$ X$_1$-Z$_1$;

Xaa$_1$ is His, Arg, Tyr, Ala, Norval, Val, Norleu or 4-imidazopropionyl;

Xaa$_2$ is Ser, Gly, Ala or Thr;

Xaa$_3$ is Ala, Asp or Glu;

Xaa$_4$ is Ala, Norval, Val, Norleu or Gly;

Xaa$_5$ is Ala or Thr;

Xaa$_6$ is Phe, Tyr or naphthylalanine;

Xaa$_7$ is Thr or Ser;

Xaa$_8$ is Ala, Ser or Thr;

Xaa$_9$ is Ala, Norval, Val, Norleu, Asp or Glu;

Xaa$_{10}$ is Ala, Leu, Ile, Val, pentylglycine or Met;

Xaa$_{11}$ is Ala or Ser;

Xaa$_{12}$ is Ala or Lys;

Xaa$_{13}$ is Ala or Gln;

Xaa$_{14}$ is Ala, Leu, Ile, pentylglycine, Val or Met;

Xaa$_{15}$ is Ala or Glu;

Xaa$_{16}$ is Ala or Glu;

Xaa$_{17}$ is Ala or Glu;

Xaa$_{19}$ is Ala or Val;

Xaa$_{20}$ is Ala or Arg;

Xaa$_{21}$ is Ala, Leu or Lys-NH$^\epsilon$-R where R is Lys, Arg, C$^-$$^C$10 straight chain or branched alkanoyl or cycloalleyl-alkanoyl;

Xaa$_{22}$ is Phe, Tyr or naphthylalanine;

Xaa$_{23}$ is Ile, Val, Leu, pentylglycine, tert-butylglycine or Met;

Xaa$_{24}$ is Ala, Glu or Asp;

Xaa$_{25}$ is Ala, Trp, Phe, Tyr or naphthylalanine;

Xaa$_{26}$ is Ala or Leu;

X$_1$ is Lys Asn, Asn Lys, Lys-NH$^\epsilon$-R Asn, Asn Lys-NH$^\epsilon$-R, Lys-NH$^\epsilon$-R Ala, Ala Lys-NH$^\epsilon$-R where R is Lys, Arg, C$_1$–C$_{10}$ straight chain or branched alkanoyl or cycloalkylalkanoyl Z$_1$ is

—OH,

—NH$_2$,

Gly-Z$_2$,

Gly Gly-Z$_2$,

-continued

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$,

Gly Gly Xaa$_{31}$ Ser Ser Gly Ala Xaa$_{36}$ Xaa$_{37}$ Xaa$_{38}$-Z$_2$ or

Gly Gly Xaa$_{31}$ Ser Ser Gly Ala Xaa$_{36}$ Xaa$_{37}$ Xaa$_{38}$ Xaa$_{39}$-Z$_2$;

wherein

Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; and Z$_2$ is –0 or —NH$_2$;

provided that no more than three of Xaa$_{31}$ Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, are Ala; and provided also that, if Xaa$_1$ is His, Arg, Tyr, or 4-imidazopropionyl then at least one of Xaa$_3$, Xaa$_4$ and Xaa$_9$ is Ala.

Also within the scope of the present invention are pharmaceutically acceptable salts of the compounds of formula (II) and pharmaceutical compositions including said compounds and salts hereof.

Preferred compounds of formula (II) include those wherein Xaa$_1$ is His, Ala, Norval or 4-imidazopropionyl. Preferably, Xaa$_1$ is His, or 4-imidazopropionyl or Ala, more preferably His or 4-imidazopropionyl.

Preferred compounds of formula (II) include those wherein Xaa$_2$ is Gly.

Preferred compounds of formula (II) include those wherein Xaa$_4$ is Ala.

Preferred compounds of formula (II) include those wherein Xaa$_9$ is Ala.

Preferred compounds of formula (II) include those wherein Xaa$_{14}$ is Leu, pentylglycine or Met.

Preferred compounds of formula (II) include those wherein Xaa$_{25}$ is Trp or Phe.

Preferred compounds of formula (II) include those wherein Xaa$_6$ is Ala, Phe or naphthylalanine; Xaa$_{22}$ is Phe or naphthylalanine; and Xaa$_{23}$ is Ile or Val.

Preferred compounds of formula (II) include those wherein Z$_1$ is —NH$_2$.

Preferred compounds of formula (II) include those wherein Xaa$_{31}$, Xaa$_{36}$, Xaa$_{37}$ and Xaa$_{38}$ are independently selected from the group consisting of Pro, homoproline, thioproline and N-alkylalanine.

Preferred compounds of formula (II) include those wherein Xaa$_{39}$ is Ser or Tyr, preferably Ser.

Preferred compounds of formula (II) include those wherein Z$_2$ is —NH$_2$.

Preferred compounds of formula (II) include those 42 wherein Z$_1$ is —NH$_2$.

Preferred compounds of formula (II) include those wherein Xaa$_{21}$ is Lys-NH$^\epsilon$-R where R is Lys, Arg, C$_1$–C$_{10}$ straight chain or branched alkanoyl.

Preferred compounds of formula (II) include those wherein X$_1$ is Lys Asn, Lys-NH$^\epsilon$-R Asn, or Lys-NH$^\epsilon$-R Ala where R is Lys, Arg, C$_1$–C$_{10}$ straight chain or branched alkanoyl.

Preferred compounds of formula (II) include those having an amino acid sequence selected from SEQ. ID. NOS. 95–110.

The compounds referenced above form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Utility

The compounds described above are useful in view of their pharmacological properties. In particular, the compounds of the invention are exendin agonists, and possess activity as agents to regulate gastric motility and to slow gastric emptying, as evidenced by the ability to reduce post-prandial glucose levels in mammals.

The compounds of the present invention are useful in in vitro and in vivo scientific methods for investigation of exendins and exendin agonists for example in methods such as those described in Examples A–E below.

Preparation of Compounds

The compounds of the present invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser (Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu (t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods.

Formulation and Administration

Compounds of the invention are useful in view of their exendin-like effects, and may conveniently be provided in the form of formulations suitable for parenteral (including intravenous, intramuscular and subcutaneous) or nasal, buccal or oral administration. In some cases, it will be convenient to provide an exendin agonist and another anti-gastric-emptying agent, such as glucagon, an amylin, or an amylin agonist, in a single composition or solution for administration together. In other cases, it may be more advantageous to administer another anti-emptying agent separately from said exendin agonist. In yet other cases, it may be beneficial to provide an exendin agonist either co-formulated or separately with other glucose lowering agents such as insulin. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or other form of delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compounds will be provided in dosage unit form containing an amount of an exendin agonist, with or without another anti-emptying agent. Therapeutically effective amounts of an exendin agonist for use in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels, may be obtained. As will be recognized by those in the field, an effective amount of therapeutic agent will vary with many factors including the patient's physical condition, the blood sugar level or level of inhibition of gastric emptying to be obtained, and other factors.

Such pharmaceutical compositions are useful in causing gastric hypomotility in a subject and may be used as well in other disorders where gastric motility is beneficially reduced.

The effective daily anti-emptying dose of the compounds will typically be in the range of 0.001 or 0.005 to about 5 mg/day, preferably about 0.01 or 0.05 to 2 mg/day and more preferably about 0.05 or 0.1 to 1 mg/day, for a 70 kg patient. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus. Administration may be by injection, preferably subcutaneous or intramuscular. Administration may also be by other routes, for example, by oral, buccal or nasal routes, however dosages should be increased about 5–10 fold, over injection doses.

Generally, in treating or preventing elevated, inappropriate, or undesired post-prandial blood glucose levels, the compounds of this invention may be administered to patients in need of such treatment in a dosage ranges similar to those given above, however, the compounds are administered more frequently, for example, one, two, or three times a day.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Preparation of Compound 1

```
                                          [SEQ. ID. NO. 5]
Ala Gly Glu Gly Thr Phe Thr Ser Asp Leu Ser Lys Gln

Leu Glu Glu Glu Ala Val Arg Leu Phe Ile Glu Phe Leu

Lys Asn-NH₂
```

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 19.2 minutes. Electrospray Mass Spectrometry (M): calculated 3171.6; found 3172.

EXAMPLE 2

Preparation of Compound 2

[SEQ. ID. NO. 6]
His Gly Ala Gly Thr Phe Thr Ser Asp Leu Ser Lys Gln

Leu Glu Glu Glu Ala Val Arg Leu Phe Ile Glu Phe Leu

Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 14.9 minutes. Electrospray Mass Spectrometry (M): calculated 3179.6; found 3180.

EXAMPLE 3

Preparation of Compound 3

[SEQ. ID. NO. 7]
His Gly Glu Ala Thr Phe Thr Ser Asp Leu Ser Lys Gln

Leu Glu Glu Glu Ala Val Arg Leu Phe Ile Glu Phe Leu

Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 37% to 47% Solvent B in Solvent A over 30 minutes) of the lyophilized peptide gave product peptide having an observed retention time of 12.2 minutes. Electrospray Mass Spectrometry (M): calculated 3251.6; found 3253.3.

EXAMPLE 4

Preparation of Compound 4

[SEQ. ID. NO. 8]
His Gly Glu Gly Thr Phe Thr Ser Ala Leu Ser Lys Gln

Leu Glu Glu Glu Ala Val Arg Leu Phe Ile Glu Phe Leu

Lys Asn-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis were Solvent A (0.1% TFA in water) and Solvent B (0.1% TFA in ACN). Analytical RP-HPLC (gradient 35% to 45% Solvent B in Solvent A over 30 minutes) of the lyophilized peptide gave product peptide having an observed retention time of 16.3 minutes. Electrospray Mass Spectrometry (M): calculated 3193.6; found 3197.

EXAMPLE 5

Preparation of Compound 5

[SEQ. ID. NO. 9]
Ala Gly Glu Gly Thr Phe Thr Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3228.6.

EXAMPLE 6

Preparation of Compound 6

[SEQ. ID. NO. 10]
His Gly Ala Gly Thr Phe Thr Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3234.7.

EXAMPLE 7

Preparation of Compound 7

[SEQ. ID. NO. 11]
His Gly Glu Ala Thr Phe Thr Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3308.7.

EXAMPLE 8

Preparation of Compound 8

[SEQ. ID. NO. 12]
His Gly Glu Gly Thr Phe Thr Ser Ala Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3250.7

EXAMPLE 9

Preparation of Compound 9

[SEQ. ID. NO. 13]
His Gly Glu Gly Thr Phe Thr Ser Asp Ala Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3252.6.

EXAMPLE 10

Preparation of Compound 10

[SEQ. ID. NO. 14]
Ala Ala Glu Gly Thr Phe Thr Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 11

Preparation of Compound 11

[SEQ. ID. NO. 15]
Ala Ala Glu Gly Thr Phe Thr Ser Asp Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 12

Preparation of Compound 12

[SEQ. ID. NO. 16]
Ala Gly Asp Gly Thr Phe Thr Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3214.6.

EXAMPLE 13

Preparation of Compound 13

[SEQ. ID. NO. 17]
Ala Gly Asp Gly Thr Phe Thr Ser Asp Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 14

Preparation of Compound 14

[SEQ. ID. NO. 18]
Ala Gly Asp Gly Ala Phe Thr Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3184.6.

EXAMPLE 15

Preparation of Compound 15

[SEQ. ID. NO. 19]
Ala Gly Asp Gly Ala Phe Thr Ser Asp Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3127.5.

EXAMPLE 16

Preparation of Compound 16

[SEQ. ID. NO. 20]
Ala Gly Asp Gly Thr NaphthylAla Thr Ser Asp Leu Ser

Lys Gln Met Glu Glu Glu Ala Val Arg Leu Phe Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3266.4.

EXAMPLE 17

Preparation of Compound 17

[SEQ. ID. NO. 21]
Ala Gly Asp Gly Thr Naphthylala Thr Ser Asp Leu Ser

Lys Gln Leu Glu Glu Glu Ala Val Arg Leu Phe Ile Glu

Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3209.4.

EXAMPLE 18

Preparation of Compound 18

[SEQ. ID. NO. 22]
Ala Gly Asp Gly Thr Phe Ser Ser Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 19

Preparation of Compound 19

[SEQ. ID. NO. 23]
Ala Gly Asp Gly Thr Phe Ser Ser Asp Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 20

Preparation of Compound 20

[SEQ. ID. NO. 24]
Ala Gly Asp Gly Thr Phe Thr Ala Asp Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3198.6.

EXAMPLE 21

Preparation of Compound 21

[SEQ. ID. NO. 25]
Ala Gly Asp Gly Thr Phe Thr Ala Asp Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3141.5.

EXAMPLE 22

Preparation of Compound 22

[SEQ. ID. NO. 26]
Ala Gly Asp Gly Thr Phe Thr Ser Ala Leu Ser Lys Gln

Met Glu Glu Glu Ala Val Arg Leu Phe Ile Glu Trp Leu

Lys Asn-NH$_2$

The above-identified peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M) calculated 3170.6.

EXAMPLE 23

Preparation of Compound 23

[SEQ. ID. NO. 27]
Ala Gly Asp Gly Thr Phe Thr Ser Ala Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3113.5.

EXAMPLE 24

Preparation of Compound 24

[SEQ. ID. NO. 28]
Ala Gly Asp Gly Thr Phe Thr Ser Glu Leu Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3228.6.

EXAMPLE 25

Preparation of Compound 25

[SEQ. ID. NO. 29]
Ala Gly Asp Gly Thr Phe Thr Ser Glu Leu Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3171.6.

EXAMPLE 26

Preparation of Compound 26

[SEQ. ID. NO. 30]
Ala Gly Asp Gly Thr Phe Thr Ser Asp Ala Ser Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 27

Preparation of Compound 27

[SEQ. ID. NO. 31]
Ala Gly Asp Gly Thr Phe Thr Ser Asp Ala Ser Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.4.

EXAMPLE 28

Preparation of Compound 28

[SEQ. ID. NO. 32]
Ala Gly Asp Gly Thr Phe Thr Ser Asp Pentylgly Ser

Lys Gln Met Glu Glu Glu Ala Val Arg Leu Phe Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3230.4.

EXAMPLE 29

Preparation of Compound 29

[SEQ. ID. NO. 33]
Ala Gly Asp Gly Thr Phe Thr Ser Asp Pentylgly Ser

Lys Gln Leu Glu Glu Glu Ala Val Arg Leu Phe Ile Glu

Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3198.6.

EXAMPLE 30

Preparation of Compound 30

[SEQ. ID. NO. 34]
Ala Gly Asp Gly Thr Phe Thr Ser Asp Leu Ala Lys Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-=protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3141.5.

EXAMPLE 31

Preparation of Compound 31

[SEQ. ID. NO. 35]
Ala Gly Asp Gly Thr Phe Thr Ser Asp Leu Ala Lys Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 32

Preparation of Compound 32

[SEQ. ID. NO. 36]
Ala Gly Asp Gly Thr Phe Thr Ser Asp Leu Ser Ala Gln

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.4.

EXAMPLE 33

Preparation of Compound 33

[SEQ. ID. NO. 37]
Ala Gly Asp Gly Thr Phe Thr Ser Asp Leu Ser Ala Gln

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA

EXAMPLE 34

Preparation of Compound 34

[SEQ. ID. NO. 38]
Ala Gly Asp Gly Thr Phe Thr Ser Asp Leu Ser Lys Ala

Met Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.5.

EXAMPLE 35

Preparation of Compound 35

[SEQ. ID. NO. 39]
Ala Gly Asp Gly Thr Phe Thr Ser Asp Leu Ser Lys Ala

Leu Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.5.

EXAMPLE 36

Preparation of Compound 36

[SEQ. ID. NO. 40]
Ala Gly Asp Gly Thr Phe Thr Ser Asp Leu Ser Lys Gln

Ala Glu Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3154.5.

EXAMPLE 37

Preparation of Compound 37

[SEQ. ID. NO. 41]
Ala Gly Asp Gly Thr Phe Thr Ser Asp Leu Ser Lys Gln

Ala Glu Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 38

Preparation of Compound 38

[SEQ. ID. NO. 42]
Ala Gly Asp Gly Thr Phe Thr Ser Asp Leu Ser Lys Gln

Pentylgly Glu Glu Glu Ala Val Arg Leu Phe Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3212.4.

EXAMPLE 39

Preparation of Compound 39

[SEQ. ID. NO. 43]
Ala Gly Asp Gly Thr Phe Thr Ser Asp Leu Ser Lys Gln

Pentylgly Glu Glu Glu Ala Val Arg Leu Phe Ile Glu

Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3173.4.

EXAMPLE 40

Preparation of Compound 40

[SEQ. ID. NO. 44]
Ala Gly Asp Gly Thr Phe Thr Ser Asp Leu Ser Lys Gln

Met Ala Glu Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino-acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 41

Preparation of Compound 41

[SEQ. ID. NO. 45]
Ala Gly Asp Gly Thr Phe Thr Ser Asp Leu Ser Lys Gln

Leu Ala Glu Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 42

Preparation of Compound 42

[SEQ. ID. NO. 46]
Ala Gly Asp Gly Thr Phe Thr Ser Asp Leu Ser Lys Gln

Met Glu Ala Glu Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 43

Preparation of Compound 43

[SEQ. ID. NO. 47]
Ala Gly Asp Gly Thr Phe Thr Ser Asp Leu Ser Lys Gln

Leu Glu Ala Glu Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 44

Preparation of Compound 44

[SEQ. ID. NO. 48]
Ala Gly Asp Gly Thr Phe Thr Ser Asp Leu Ser Lys Gln

Met Glu Glu Ala Ala Val Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3156.6.

EXAMPLE 45

Preparation of Compound 45

[SEQ. ID. NO. 49]
Ala Gly Asp Gly Thr Phe Thr Ser Asp Leu Ser Lys Gln

Leu Glu Glu Ala Ala Val Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 46

Preparation of Compound 46

[SEQ. ID. NO. 50]
Ala Gly Asp Gly Thr Phe Thr Ser Asp Leu Ser Lys Gln

Met Glu Glu Glu Ala Ala Arg Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA-resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3186.6.

EXAMPLE 47

Preparation of Compound 47

[SEQ. ID. NO. 51]
Ala Gly Asp Gly Thr Phe Thr Ser Asp Leu Ser Lys Gln

Leu Glu Glu Glu Ala Ala Arg Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3129.5.

EXAMPLE 48

Preparation of Compound 48

[SEQ. ID. NO. 52]
Ala Gly Asp Gly Thr Phe Thr Ser Asp Leu Ser Lys Gln

Met Glu Glu Glu Ala Val Ala Leu Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3129.5.

EXAMPLE 49

Preparation of Compound 49

[SEQ. ID. NO. 53]
Ala Gly Asp Gly Thr Phe Thr Ser Asp Leu Ser Lys Gln

Leu Glu Glu Glu Ala Val Ala Leu Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA-resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA

EXAMPLE 50

Preparation of Compound 50

[SEQ. ID. NO. 54]
Ala Gly Asp Gly Thr Phe Thr Ser Asp Leu Ser Lys Gln

Met Glu Glu Glu Ala Val Arg Ala Phe Ile Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 51

Preparation of Compound 51

[SEQ. ID. NO. 55]
Ala Gly Asp Gly Thr Phe Thr Ser Asp Leu Ser Lys Gln

Leu Glu Glu Glu Ala Val Arg Ala Phe Ile Glu Phe Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 52

Preparation of Compound 52

[SEQ. ID. NO. 56]
Ala Gly Asp Gly Thr Phe Thr Ser Asp Leu Ser Lys Gln

Met Glu Glu Glu Ala Val Arg Leu Naphthylala Ile Glu

Trp Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3266.4.

EXAMPLE 53

Preparation of Compound 53

[SEQ. ID. NO. 57]
Ala Gly Asp Gly Thr Phe Thr Ser Asp Leu Ser Lys Gln

Leu Glu Glu Glu Ala Val Arg Leu Naphthylala Ile Glu

Phe Leu Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3209.4.

EXAMPLE 54

Preparation of Compound 54

[SEQ. ID. NO. 58]
Ala Gly Asp Gly Thr Phe Thr Ser Asp Leu Ser Lys Gln

Met Glu Glu Glu Ala Val Arg Leu Phe Val Glu Trp Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 55

Preparation of Compound 55

[SEQ. ID. NO. 59]
Ala Gly Asp Gly Thr Phe Thr Ser Asp Leu Ser Lys Gln
Leu Glu Glu Glu Ala Val Arg Leu Phe Val Glu Phe Leu
Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 56

Preparation of Compound 56

[SEQ. ID. NO. 60]
Ala Gly Asp Gly Thr Phe Thr Ser Asp Leu Ser Lys Gln
Met Glu Glu Glu Ala Val Arg Leu Phe tButylgly Glu
Trp Leu Lys Asn-NH$_2$ The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3216.5.

EXAMPLE 57

Preparation of Compound 57

[SEQ. ID. NO. 61]
Ala Gly Asp Gly Thr Phe Thr Ser Asp Leu Ser Lys Gln
Leu Glu Glu Glu Ala Val Arg Leu Phe tButylgly Glu
Phe Leu Lys Asn-NH$_2$ The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3159.4.

EXAMPLE 58

Preparation of Compound 58

[SEQ. ID. NO. 62]
Ala Gly Asp Gly Thr Phe Thr Ser Asp Leu Ser Lys Gln
Met Glu Glu Glu Ala Val Arg Leu Phe Ile Asp Trp Leu
Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3200.6.

EXAMPLE 59

Preparation of Compound 59

[SEQ. ID. NO. 63]
Ala Gly Asp Gly Thr Phe Thr Ser Asp Leu Ser Lys Gln
Leu Glu Glu Glu Ala Val Arg Leu Phe Ile Asp Phe Leu
Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3143.5.

EXAMPLE 60

Preparation of Compound 60

[SEQ. ID. NO. 64]
Ala Gly Asp Gly Thr Phe Thr Ser Asp Leu Ser Lys Gln
Met Glu Glu Glu Ala Val Arg Leu Phe Ile Glu Ala Leu
Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3099.5.

EXAMPLE 61

Preparation of Compound 61

[SEQ. ID. NO. 65]
Ala Gly Asp Gly Thr Phe Thr Ser Asp Leu Ser Lys Gln

Leu Glu Glu Glu Ala Val Arg Leu Phe Ile Glu Ala Leu

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3081.4.

EXAMPLE 62

Preparation of Compound 62

[SEQ. ID. NO. 66]
Ala Gly Asp Gly Thr Phe Thr Ser Asp Leu Ser Lys Gln

Met Glu Glu Glu Ala Val Arg Leu Phe Ile Glu Trp Ala

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3172.5.

EXAMPLE 63

Preparation of Compound 63

[SEQ. ID. NO. 67]
Ala Gly Asp Gly Thr Phe Thr Ser Asp Leu Ser Lys Gln

Leu Glu Glu Glu Ala Val Arg Leu Phe Ile Glu Phe Ala

Lys Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3115.5.

EXAMPLE 64

Preparation of Compound 64

[SEQ. ID. NO. 68]
Ala Gly Asp Gly Thr Phe Thr Ser Asp Leu Ser Lys Gln

Met Glu Glu Glu Ala Val Arg Leu Phe Ile Glu Trp Leu

Ala Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3157.5.

EXAMPLE 65

Preparation of Compound 65

[SEQ. ID. NO. 69]
Ala Gly Asp Gly Thr Phe Thr Ser Asp Leu Ser Lys Gln

Leu Glu Glu Glu Ala Val Arg Leu Phe Ile Glu Phe Leu

Ala Asn-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA

EXAMPLE 66

Preparation of Compound 66

[SEQ. ID. NO. 70]
Ala Gly Asp Gly Thr Phe Thr Ser Asp Leu Ser Lys Gln

Met Glu Glu Glu Ala Val Arg Leu Phe Ile Glu Trp Leu

Lys Ala-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3171.6.

EXAMPLE 67

Preparation of Compound 67

[SEQ. ID. NO. 71]
Ala Gly Asp Gly Thr Phe Thr Ser Asp Leu Ser Lys Gln

Leu Glu Glu Glu Ala Val Arg Leu Phe Ile Glu Phe Leu

Lys Ala-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3114.5.

EXAMPLE 68

Preparation of Compound 68

[SEQ. ID. NO. 72]
Ala Gly Glu Gly Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly Ala Pro Pro Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3100.4.

in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4033.5.

EXAMPLE 69

Preparation of Compound 69

[SEQ. ID. NO. 73]
His Gly Ala Gly Thr Phe Thr Ser Asp Leu Ser Lys Gln

Leu Glu Glu Glu Ala Val Arg Leu Phe Ile Glu Phe Leu

Lys Asn Gly Gly Pro Ser Ser Gly Ala Pro Pro Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3984.4.

EXAMPLE 70

Preparation of Compound 70

[SEQ. ID. NO. 74]
His Gly Glu Ala Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly Ala Pro Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4016.5.

EXAMPLE 71

Preparation of Compound 71

[SEQ. ID. NO. 75]
His Gly Glu Gly Thr Phe Thr Ser Ala Leu Ser Lys Gln

Met Glu Glu Glu Ala Val Arg Leu Phe Ile Glu Trp Leu

Lys Asn Gly Gly Pro Ser Ser Gly Ala Pro-$NH_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3861.3.

EXAMPLE 72

Preparation of Compound 72

[SEQ. ID. NO. 76]
Ala Gly Glu Gly Thr Phe Thr Ser Asp Ala Ser Lys Gln

Leu Glu Glu Glu Ala Val Arg Leu Phe Ile Glu Phe Leu

Lys Asn Gly Gly Pro Ser Ser Gly Ala Pro-$NH_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3746.1.

EXAMPLE 73

Preparation of Compound 73

[SEQ. ID. NO. 77]
Ala Gly Glu Gly Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly Ala-$NH_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3742.1.

EXAMPLE 74

Preparation of Compound 74

[SEQ. ID. NO. 78]
His Gly Ala Gly Thr Phe Thr Ser Asp Leu Ser Lys Gln

Leu Glu Glu Glu Ala Val Arg Leu Phe Ile Glu Phe Leu

Lys Asn Gly Gly Pro Ser Ser Gly Ala-$NH_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3693.1.

EXAMPLE 75

Preparation of Compound 75

[SEQ. ID. NO. 79]
His Gly Glu Ala Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly-$NH_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3751.2.

EXAMPLE 76

Preparation of Compound 76

[SEQ. ID. NO. 80]
His Gly Glu Gly Thr Phe Thr Ser Ala Leu Ser Lys Gln

Met Glu Glu Glu Ala Val Arg Leu Phe Ile Glu Trp Leu

Lys Asn Gly Gly Pro Ser Ser-$NH_2$

51

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3634.1.

EXAMPLE 77

Preparation of Compound 77

[SEQ. ID. NO. 81]
Ala Gly Glu Gly Thr Phe Thr Ser Asp Leu Ser Lys Gln

Met Glu Glu Glu Ala Val Arg Leu Phe Ile Glu Trp Leu

Lys Asn Gly Gly Pro Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3526.9.

EXAMPLE 78

Preparation of Compound 78

[SEQ. ID. NO. 82]
His Gly Ala Gly Thr Phe Thr Ser Asp Leu Ser Lys Gln

Leu Glu Glu Glu Ala Val Arg Leu Phe Ile Glu Phe Leu

Lys Asn Gly Gly Pro Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3477.9.

52

EXAMPLE 79

Preparation of Compound 79

[SEQ. ID. NO. 83]
His Gly Glu Ala Thr Phe Thr Ser Asp Leu Ser Lys Gln

Met Glu Glu Ala Val Arg Leu Phe Ile Glu Trp Leu

Lys Asn Gly Gly Pro-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3519.9.

EXAMPLE 80

Preparation of Compound 80

[SEQ. ID. NO. 84]
His Gly Glu Gly Thr Phe Thr Ser Ala Leu Ser Lys Gln

Leu Glu Glu Glu Ala Val Arg Leu Phe Ile Glu Phe Leu

Lys Asn Gly Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3307.7.

EXAMPLE 81

Preparation of Compound 81

[SEQ. ID. NO. 85]
Ala Gly Glu Gly Thr Phe Thr Ser Asp Leu Ser Lys Gln

Leu Glu Glu Glu Ala Val Arg Leu Phe Ile Glu Phe Leu

Lys Asn Gly-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3186.5.

EXAMPLE 82

Preparation of Compound 82

[SEQ. ID. NO. 86]
His Gly Ala Gly Thr Phe Thr Ser Asp Leu Ser Lys Gln

Met Glu Glu Glu Ala Val Arg Leu Phe Ile Glu Trp Leu

Lys Asn Gly Gly tPro Ser Ser Gly Ala tPro tPro tPro-NH₂

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4121.1.

EXAMPLE 83

Preparation of Compound 83

[SEQ. ID. NO. 87]
His Gly Glu Ala Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly Ala tPro tPro tPro-NH₂

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 37, 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4173.2.

EXAMPLE 84

Preparation of Compound 84

[SEQ. ID. NO. 88]
His Gly Glu Gly Thr Phe Thr Ser Ala Leu Ser Lys Gln

Met Glu Glu Glu Ala Val Arg Leu Phe Ile Glu Trp Leu

Lys Asn Gly Gly NMeala Ser Ser Gly Ala NMeala

Nmeala-NH₂

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Double couplings are required at residues 36 and 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3796.1.

EXAMPLE 85

Preparation of Compound 85

[SEQ. ID. NO. 89]
Ala Gly Glu Gly Thr Phe Thr Ser Asp Leu Ser Lys Gln

Met Glu Glu Glu Ala Val Arg Leu Phe Ile Glu Trp Leu

Lys Asn Gly Gly hPro Ser Ser Gly Ala hPro-NH₂

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. A double coupling is required at residue 31. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3871.1.

EXAMPLE 86

Preparation of Compound 86

[SEQ. ID. NO. 90]
His Gly Ala Gly Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly Ala-NH₂

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3750.2.

EXAMPLE 87

Preparation of Compound 87

[SEQ. ID. NO. 91]
His Gly Asp Ala Thr Phe Thr Ser Asp Leu Ser Lys Gln

Met Glu Glu Glu Ala Val Arg Leu Phe Ile Glu Trp Leu

Lys Asn Gly Gly-NH$_2$

The above-identified amdiated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3408.8.

EXAMPLE 88

Preparation of Compound 88

[SEQ. ID. NO. 92]
Ala Gly Glu Gly Thr Phe Thr Ser Asp Leu Ser Lys Gln

Met Glu Glu Glu Ala Val Arg Leu Phe Ile Glu Trp Leu

Lys Asn Gly Gly Pro Ser Ser Gly Ala Pro Pro Pro

Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4120.6.

EXAMPLE 89

Preparation of Compound 89

[SEQ. ID. NO. 93]
Ala Gly Ala Gly Thr Phe Thr Ser Asp Leu Ser Lys Gln

Leu Glu Glu Glu Ala Val Arg Leu Phe Ile Glu Phe Leu

Lys Asn Gly Gly Pro Ser Ser Gly Ala Pro Pro Pro

Ser-NH$_2$

The above-identified amidated peptide is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Compound 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 4005.5.

EXAMPLE 90

Preparation of Peptide Having SEQ. ID. NO. 95

Compound No. 90, 4-imidazolylpropionyl-Gly Glu Gly Thr Phe Thr Ser Ala Leu Ser Lys Gln Met Glu Glu Glu Ala Val Arg Leu Phe Ile Glu Trp Leu Lys-NH$^\epsilon$octanoyl Asn-NH$_2$ [SEQ. ID. NO. 95], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2–28 on the resin. Used in analysis are Solvent A (0.1% TFA in water) and Solvent B (0.1% TFA in CAN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3361.7

EXAMPLE 91

Preparation of Peptide Having SEQ. ID. NO. 96

Compound No. 91, 4-imidazolylpropionyl-Gly Glu Gly Thr Phe Thr Ser Ala Leu Ser Lys Gln Leu Glu Glu Glu Ala Val Arg Leu Phe Ile Glu Phe Leu Lys-NH$^\epsilon$octanoyl Asn-NH$_2$ [SEQ. ID. NO. 96], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2–28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3304.6

EXAMPLE 92

Preparation of Peptide Having SEQ. ID. NO. 97

Compound No. 92, 4-imidazolylpropionyl-Gly Glu Gly Thr Phe Thr Ser Ala Leu Ser Lys Gln Met Glu Glu Glu Ala Val Arg Leu Phe Ile Glu Trp Leu Lys-NH$^\epsilon$octanoyl Asn Gly Gly-NH$_2$ [SEQ. ID. NO. 97], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2–30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3475.8

EXAMPLE 93

Preparation of Peptide Having SEQ. ID. NO. 98

Compound No. 93, 4-imidazolylpropionyl-Gly Glu Gly Thr Phe Thr Ser Ala Leu Ser Lys Gln Leu Glu Glu Glu Ala Val Arg Leu Phe Ile Glu Phe Leu Lys-NH$^\epsilon$octanoyl Asn Gly Gly-NH$_2$ [SEQ. ID. NO. 98], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Instead of using a protected amino acid for the final coupling at position 1, 4-imidazolylpropionic acid is coupled directly to the N-terminus of residues 2–30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3418.7

EXAMPLE 94

Preparation of Peptide Having SEQ. ID. NO. 99

Compound No. 94, 4-imidazolylpropionyl-Gly Glu Gly Thr Phe Thr Ser Ala Leu Ser Lys Gln Met Glu Glu Glu Ala Val Arg Leu Phe Ile Glu Trp Leu Asn Lys-NH$^\epsilon$octanoyl-NH$_2$ [SEQ. ID. NO. 99], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for the initial coupling onto the resin at position 28. Instead of using a protected amino acid for the final coupling at position 1, 4-imidazolylpropionic acid is coupled directly to the N-terminus of protected residues 2–28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3361.7

EXAMPLE 95

Preparation of Peptide Having SEQ. ID. NO. 100

Compound No. 95, 4-imidazolylpropionyl-Gly Glu Gly Thr Phe Thr Ser Ala Leu Ser Lys Gln Leu Glu Glu Glu Ala Val Arg Leu Phe Ile Glu Phe Leu Asn Lys-NH$^\epsilon$octanoyl-NH$_2$ [SEQ. ID. NO. 100], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for the initial coupling onto the resin at position 28. Instead of using a protected amino acid for the final coupling at position 1, 4-imidazolylpropionic acid is coupled directly to the N-terminus of residues 2–28 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3304.6

EXAMPLE 96

Preparation of Peptide Having SEQ. ID. NO. 101

Compound 96, 4-imidazolylpropionyl-Gly Glu Gly Thr Phe Thr Ser Ala Leu Ser Lys Gln Met Glu Glu Glu Ala Val Arg Leu Phe Ile Glu Trp Leu Asn Lys-NH$^\epsilon$octanoyl Gly Gly-NH$_2$ [SEQ. ID. NO. 101], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 28. Instead of using a protected amino acid for the final coupling at position 1, 4-imidazolylpropionic acid is coupled directly to the N-terminus of protected residues 2–30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3475.8

EXAMPLE 97

Preparation of Peptide Having SEQ. ID. NO. 102

Compound No. 97, 4-imidazolylpropionyl-Gly Glu Gly Thr Phe Thr Ser Ala Leu Ser Lys Gln Leu Glu Glu Glu Ala Val Arg Leu Phe Ile Glu Phe Leu Asn Lys-NH$^\epsilon$octanoyl Gly Gly-NH$_2$ [SEQ. ID. NO. 102], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 28. Instead of using protected His for the final coupling at position 1, 4-imidazolylpropionic acid is coupled directly to the N-terminus of residues 2–30 on the resin. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3418.7

EXAMPLE 98

Preparation of Peptide Having SEQ. ID. NO. 103

Compound No. 98, Ala Gly Glu Gly Thr Phe Thr Ser Asp Leu Ser Lys Gln Met Glu Glu Glu Ala Val Arg Leu Phe Ile Glu Trp Leu Lys-NH$^\epsilon$octanoyl Asn-NH$_2$ [SEQ. ID. NO. 103], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3334.6

EXAMPLE 99

Preparation of Peptide Having SEQ. ID. NO. 104

Compound No. 99, Ala Gly Glu Gly Thr Phe Thr Ser Asp Leu Ser Lys Gln Leu Glu Glu Glu Ala Val Arg Leu Phe Ile Glu Phe Leu Lys-NH$^\epsilon$octanoyl Asn-NH$_2$ [SEQ. ID. NO. 104], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3277.6

EXAMPLE 100

Preparation of Peptide Having SEQ. ID. NO. 105

Compound No. 100, Ala Gly Glu Gly Thr Phe Thr Ser Asp Leu Ser Lys Gln Met Glu Glu Glu Ala Val Arg Leu Phe Ile Glu Trp Leu Lys-NH$^\epsilon$octanoyl Asn Gly Gly-NH$_2$ [SEQ. ID. NO. 105], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3442.8

EXAMPLE 101

Preparation of Peptide Having SEQ. ID. NO. 106

Compound No. 101, Ala Gly Glu Gly Thr Phe Thr Ser Asp Leu Ser Lys Gln Leu Glu Glu Glu Ala Val Arg Leu Phe Ile Glu Phe Leu Lys-NH$^\epsilon$octanoyl Asn Gly Gly-NH$_2$ [SEQ. ID. NO. 106], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 27. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3391.7

EXAMPLE 102

Preparation of Peptide Having SEQ. ID. NO. 107

Compound No. 102, Ala Gly Glu Gly Thr Phe Thr Ser Asp Leu Ser Lys Gln Met Glu Glu Glu Ala Val Arg Leu Phe Ile Glu Trp Leu Asn Lys-NH$^\epsilon$octanoyl-NH$_2$ [SEQ. ID. NO. 107], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for the initial coupling onto the resin at position 28. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3334.6

EXAMPLE 103

Preparation of Peptide Having SEQ. ID. NO. 108

Compound No. 103, Ala Gly Glu Gly Thr Phe Thr Ser Asp Leu Ser Lys Gln Leu Glu Glu Glu Ala Val Arg Leu Phe Ile Glu Phe Leu Asn Lys-NH$^\epsilon$octanoyl-NH$_2$ [SEQ. ID. NO. 108], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for the initial coupling onto the resin at position 28. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3277.6

EXAMPLE 104

Preparation of Peptide Having SEQ. ID. NO. 109

Compound No. 104, Ala Gly Glu Gly Thr Phe Thr Ser Asp Leu Ser Lys Gln Met Glu Glu Glu Ala Val Arg Leu Phe Ile Glu Trp Leu Asn Lys-NH$^\epsilon$octanoyl Gly Gly-NH$_2$ [SEQ. ID. NO. 109], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 28. Used in analysis are Solvent A (0.1% TFA in water) and Solvent B (0.1% TFA in ACN). Analytical RP-HPLC (gradient 30% to 60 Solvent B in Solvent A over 30 minutes) of the lyophilized peptide is then carried out to determine the retention time of the product peptide. Electrospray Mass Spectrometry (M): calculated 3442.8

EXAMPLE 105

Preparation of Peptide Having SEQ. ID. NO. 110

Compound No. 105, Ala Gly Glu Gly Thr Phe Thr Ser Asp Leu Ser Lys Gln Leu Glu Glu Glu Ala Val Arg Leu Phe Ile Glu Phe Leu Asn Lys-NH$^\epsilon$octanoyl Gly Gly-NH$_2$ [SEQ. ID. NO. 110], is assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Example 1. Fmoc-Lys-NH$^\epsilon$octanoyl acid is used for coupling at position 28. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry (M): calculated 3391.7

EXAMPLE 106

Preparation of C-Terminal Carboxylic Acid Peptides Corresponding to the Above C-Terminal Amide Sequences for Compounds 1–67, 73–79, 80–81, 86–89 and 90–105

C-terminal carboxylic acid peptides corresponding to amidated Compounds 1–67, 73–79, 80–81, 86–89 and 90–105 are assembled on the so called Wang resin (p-alkoxybenzylalcohol resin (Bachem, 0.54 mmole/g)) using Fmoc-protected amino acids (Applied Biosystems, Inc.), cleaved from the resin, deprotected and purified in a similar way to that described in Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLE 107

Preparation of C-Terminal Carboxylic Acid Peptides Corresponding to the Above C-Terminal Amide Sequences for Compounds 68–72, 79 and 82–85.

C-terminal carboxylic acid peptides corresponding to amidated Compounds 68–72, 79 and 82–85 are assembled on the 2-chlorotritylchloride resin (200–400 mesh), 2% DVB (Novabiochem, 0.4–1.0 mmole/g)) using Fmoc-protected amino acids (Applied Biosystems, Inc.), cleaved from the resin, deprotected and purified in a similar way to that described in Example 1. Used in analysis are Solvent A (0.1% TFA in water) and Solvent B (0.1% TFA in ACN). Analytical RP-HPLC (gradient 30% to 60% Solvent B in Solvent A over 30 minutes) of the lyophilized peptide is then carried out to determine the retention time of the product peptide. Electrospray Mass Spectrometry provides an experimentally determined (M).

EXAMPLES A TO E

Reagents Used

GLP-1[7–36]NH$_2$ (GLP-1) was purchased from Bachem (Torrance, Calif.). All other peptides were prepared using synthesis methods such as those described therein. All chemicals were of the highest commercial grade. The cAMP SPA immunoassay was purchased from Amersham. The radioligands were purchased from New England Nuclear (Boston, Mass.). RINm5f cells (American Type Tissue Collection, Rockville, Md.) were grown in DME/F12 medium containing 10% fetal bovine serum and 2 mM L-glutamine. Cells were grown at 37° C. and 5% CO$_2$/95% humidified air and medium was replaced every 2 to 3 days. Cells were grown to confluence then harvested and homogenized using on a Polytron homogenizer. Cell homogenates were stored frozen at –70° C. until used.

EXAMPLE A

GLP-1 Receptor Binding Studies

Receptor binding was assessed by measuring displacement of [$^{125}$I]GLP-1 or [$^{125}$I]exendin (9–39) from RINm5f membranes. Assay buffer contained 5 µg/ml bestatin, 1 µg/ml phosphoramidon, 1 mg/ml bovine serum albumin (fraction V), 1 mg/ml bacitracin, and 1 mM MgCl$_2$ in 20 mM HEPES, pH 7.4. To measure binding, 30 µg membrane protein (Bradford protein assay) was resuspended in 200 µl assay buffer and incubated with 60 pM [$^{125}$I]GLP-1 or [$^{125}$I]exendin (9–39) and unlabeled peptides for 120 minutes at 23° C. in 96 well plates (Nagle Nunc, Rochester, N.Y.). Incubations were terminated by rapid filtration with cold phosphatebuffered saline, pH 7.4, through polyethyleneimine-treated GF/B glass fiber filters (Wallac Inc., Gaithersburg, Md.) using a Tomtec Mach II plate harvester (Wallac Inc., Gaithersburg, Md.). Filters were dried, combined with scintillant, and radioactivity determined in a Betaplate liquid scintillation counter (Wallac Inc.).

Peptide samples were run in the assay as duplicate points at 6 dilutions over a concentration range of $10^{-6}$M to $10^{-12}$M to generate response curves. The biological activity of a sample is expressed as an IC$_{50}$ value, calculated from the raw data using an iterative curve-fitting program using a 4-parameter logistic equation (Prizm™, GraphPAD Software). The results are shown in Table I.

TABLE I

| Compound | IC$_{50}$(nM) |
| --- | --- |
| Exendin-4 [SEQ. ID. NO. 2] | 0.7 |
| Compound 1 [SEQ. ID. NO. 5] | 26.1 |
| Compound 2 [SEQ. ID. NO. 6] | 14.42 |

TABLE I-continued

| Compound | IC$_{50}$(nM) |
|---|---|
| Compound 3 [SEQ. ID. NO. 7] | 41.65 |
| Compound 4 [SEQ. ID. NO. 8] | 4.96 |

EXAMPLE B

Cyclase Activation Study

Assay buffer contained 10 μM GTP, 0.75 mM ATP, 2.5 mM MgCl$_{21}$ 0.5 mM phosphocreatine, 12.5 U/ml creatine kinase, 0.4 mg/ml aprotinin, 1 μM IBMX in 50 mM HEPES, pH 7.4. Membranes and peptides were combined in 100 ml of assay buffer in 96 well filter-bottom plates (Millipore Corp., Bedford, Mass.). After 20 minutes incubation at 37° C., the assay was terminated by transfer of supernatant by filtration into a fresh 96 well plate using a Millipore vacuum manifold. Supernatant cAMP contents were quantitated by SPA immunoassay.

Peptide samples were run in the assay as triplicate points at 7 dilutions over a concentration range of $10^{-6}$M to $10^{-12}$M to generate response curves. The biological activity of a particular sample was expressed as an EC$_{50}$ value, calculated as described above. Results are tabulated in Table II.

TABLE II

| Compound | EC$_{50}$(nM) |
|---|---|
| Exendin-4 [SEQ. ID. NO. 2] | 0.23 |
| Compound 1 [SEQ. ID. NO. 5] | >1,000 |
| Compound 2 [SEQ. ID. NO. 6] | >10,000 |
| Compound 3 [SEQ. ID. NO. 7] | >10,000 |
| Compound 4 [SEQ. ID. NO. 8] | >10,000 |

EXAMPLE C

Determination of Blood Glucose Levels in db/db Mice

C57BLKS/J-m-db mice at least 3 months of age were utilized for the study. The mice were obtained from The Jackson Laboratory and allowed to acclimate for at least one week before use. Mice were housed in groups of ten at 22°±1° C. with a 12:12 light:dark cycle, with lights on at 6 a.m. All animals were deprived of food for 2 hours before taking baseline blood samples. Approximately 70 μl of blood was drawn from each mouse via eye puncture, after a light anesthesia with metophane. After collecting baseline blood samples, to measure plasma glucose concentrations, all animals receive subcutaneous injections of either vehicle (10.9% NaCl), exendin-4 or test compound (1 μg) in vehicle. Blood samples were drawn again, using the same procedure, after exactly one hour from the injections, and plasma glucose concentrations were measured.

For each animal, the % change in plasma value, from baseline value, was calculated. The percent decrease in plama glucose after one hour is shown in Table III.

TABLE III

| Test Compound | % drop in glucose |
|---|---|
| Exendin-4 [SEQ. ID. NO. 2] | 39% (n = 78) |
| Compound 1 [SEQ. ID. NO. 5] | 40% (n = 4) |
| Compound 2 [SEQ. ID. NO. 6] | 41% (n = 5) |
| Compound 3 [SEQ. ID. NO. 7] | 32% (n = 5) |
| Compound 4 [SEQ. ID. NO. 8] | 42% (n = 5) |

EXAMPLE D

Dose Response Determination of Blood Glucose Levels in db/db Mice

C57BLKS/J-m-db/db mice, at least 3 months of age were utilized for the study. The mice were obtained from The Jackson Laboratory and allowed to acclimate for at least one week before use. Mice were housed in groups of ten at 22° C. 1° C. with a 12:12 light:dark cycle, with lights on at 6 a.m.

All animals were deprived of food for 2 hours before taking baseline blood samples. Approximately 70 μl of blood was drawn from each mouse via eye puncture, after a light anesthesia with metophane. After collecting baseline blood samples, to measure plasma glucose concentrations, all animals receive subcutaneous injections of either vehicle, exendin-4 or test compound in concentrations indicated. Blood samples were drawn again, using the same procedure, after exactly one hour from the injections, and plasma glucose concentrations were measured.

For each animal, the % change in plasma value, from baseline value, was calculated and a dose dependent relationship was evaluated using Graphpad Prizm™ software.

FIG. 5 depicts the effects of varying doses of exendin-4 [SEQ. ID. NO. 2] and Compound 1 [SEQ. ID. NO. 5] on plasma glucose levels. Exendin-4 had an ED$_{50}$ of 0.01 μg per mouse and Compound 1 had an ED$_{50}$ of 0.42 μg per mouse.

EXAMPLE E

Gastric Emptying

The following study was carried out to examine the effects of exendin-4 and an exendin agonist compound of the present invention on gastric emptying in rats. This experiment followed a modification of the method of Scarpignato, et al., *Arch. Int. Pharmacodyn. Ther.* 246:286–94, 1980.

Male Harlan Sprague Dawley (HSD) rats were used. All animals were housed at 22.7±0.8 C in a 12:12 hour light:dark cycle (experiments being performed during the light cycle) and were fed and watered ad libitum (Diet LM-485, Teklad, Madison, Wis.). Exendin-4 was synthesized according to standard peptide synthesis methods. The preparation of Compound 1 [SEQ. ID. NO. 5] is described in Example 1.

The determination of gastric emptying by the method described below was performed after a fast of ~20 hours to ensure that the stomach contained no chyme that would interfere with spectrophotometric absorbance measurements.

Conscious rats received by gavage, 1.5 ml of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In separate experiments on 7 rats, the stomach and small intestine were both excised and opened into an alkaline solution. The quantity of phenol red that could be recovered from the upper gastrointestinal tract within 20 minutes of gavage was 89±4%; dye which appeared to bind irrecoverably to the gut luminal surface may have accounted for the balance. To account for a maximal dye recovery of less than 100%, percent of stomach contents remaining after 20 min were expressed as a fraction of the gastric contents recovered from control rats sacrificed immediately after gavage in the same experiment. Percent gastric contents remaining= (absorbance at 20 min)/(absorbance at 0 mm)×100.

In baseline studies, with no drug treatment, gastric emptying over 20 min was determined. In dose-response studies, rats were treated with 0.01, 0.1, 0.3, 1, 10 and 100 μg of exendin-4, and 0.1, 0.3, 1, 10 and 100 μg of Compound 1 [SEQ. ID. NO. 5].

Figure 6:
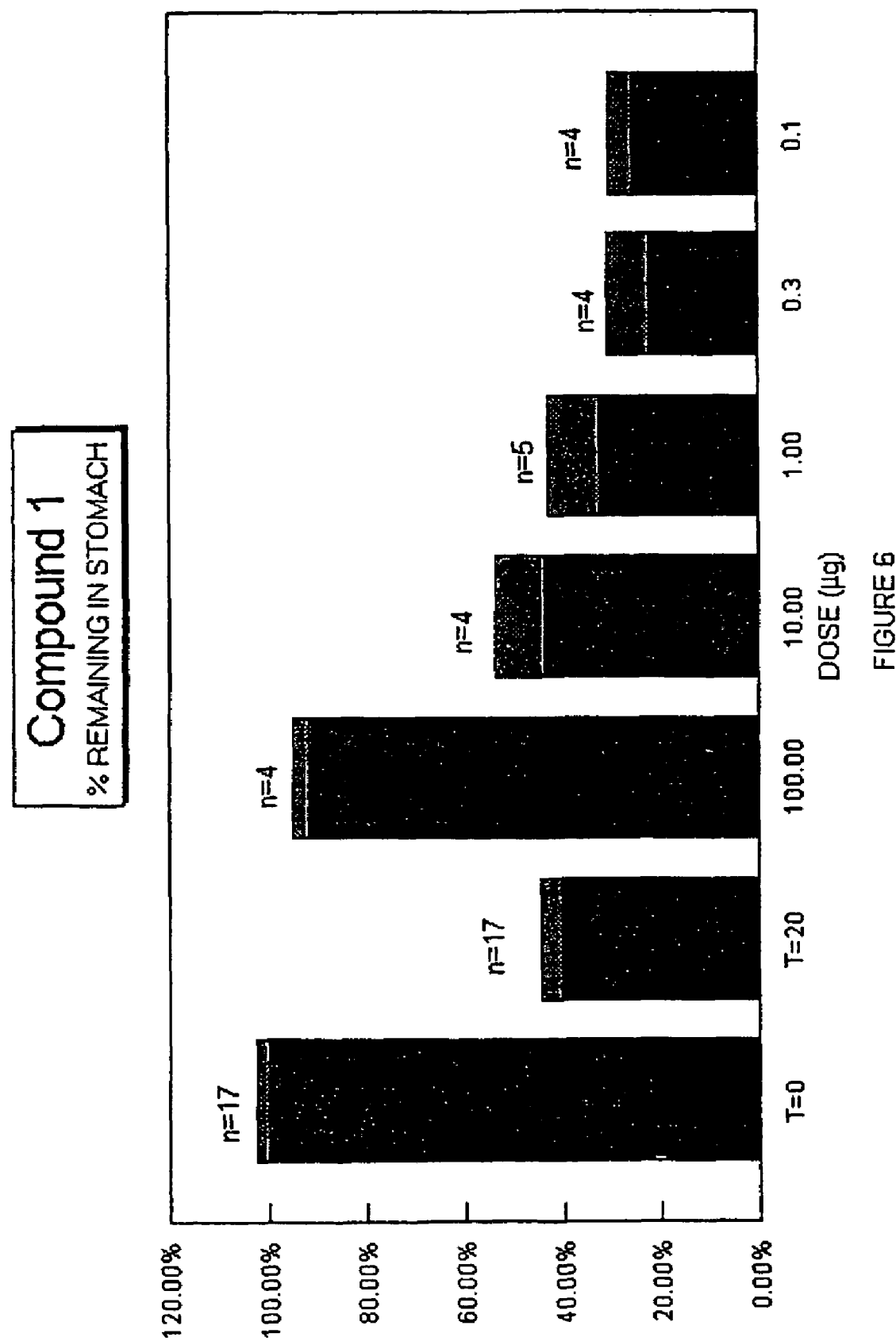
FIG. 6 depicts a comparison of effects on gastric emptying of various concentrations of Compound 1 [SEQ. ID. NO. 5]

The results, shown in FIG. 6, demonstrate that the exendin agonists, exendin-4 and Compound 1, are potent inhibitors of gastric emptying. The $EC_{50}$ for exendin-4 was 0.27 μg. The $EC_{50}$ for Compound 1 was 55.9 μg.

We claim:

1. A peptide compound or pharmaceutically acceptable salt, thereof, selected from:

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Xaa$_{37}$-Xaa$_{38}$-Xaa$_{39}$-Z$_2$, (SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Xaa$_{37}$-Xaa$_{38}$-Z$_2$, (residues 1–38 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Xaa$_{37}$-Z$_2$, (residues 1–37 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Z$_2$, (residues 1–36 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Z$_2$, (residues 1–35 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Z$_2$, (residues 1–34 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Z$_2$, (residues 1–33 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Z$_2$, (residues 1–32 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Z$_2$, (residues 1–31 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Z$_2$, (residues 1–30 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Z$_2$, (residues 1–29 of SEQ ID NO:4)-Z$_2$; and Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Z$_2$, (residues 1–28 of SEQ ID NO:4)-Z$_2$;

wherein:

Xaa$_1$ is His, Arg, Tyr, Ala, Norval, Val or Norleu;
Xaa$_2$ is Ser, Gly, Ala or Thr;
Xaa$_3$ and Xaa$_{24}$ are each independently Ala, Asp or Glu;
Xaa$_4$ is Ala, Norval, Val, Norleu or Gly;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Ala, Norval, Val, Norleu, Asp or Glu;
Xaa$_{10}$ and Xaa$_{14}$ are each independently Ala, Leu, Ile, Val, pentylglycine or Met;
Xaa$_{11}$ is Ala or Ser;
Xaa$_{12}$ and Xaa$_{27}$ are each independently Ala or Lys;
Xaa$_{13}$ is Ala or Gln;
Xaa$_{15}$, Xaa$_{16}$ and Xaa$_{17}$ are each independently Ala or Glu;
Xaa$_{19}$ is Ala or Val;
Xaa$_{20}$ is Ala or Arg;
Xaa$_{21}$ and Xaa$_{26}$ are each independently Ala or Leu;
Xaa$_{22}$ is Phe, Tyr or naphthylalanine;
Xaa$_{23}$ is Ile, Val, Leu, pentylglycine, tert-butylglycine or Met;
Xaa$_{25}$ is Ala, Trp, Phe, Tyr or naphthylalanine;
Xaa$_{28}$ is Ala or Asn;
Xaa$_{31}$, Xaa$_{36}$, Xaa$_{37}$, and Xaa$_{38}$ are each independently Pro, homoproline, 3Hyp, 4Hyp, thioproline, N-alkylglycine, N-alkylpentylglcine or N-alkylalanine;
X$_{39}$ is Ser or Tyr;
Z$_2$ is —OH or —NH$_2$; and
provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and provided also that if Xaa$_1$ is His, Arg or Tyr, then at least one of Xaa$_3$, Xaa$_4$ and Xaa$_9$ is Ala.

2. The compound according to claim 1 wherein Xaa$_1$ is His, Ala or Norval.

3. The compound according to claim 1 wherein Xaa$_1$ is Ala.

4. The compound according to claim 2 wherein Xaa$_1$ is Ala.

5. The compound according to claim 1 wherein Xaa$_1$ is His.

6. The compound according to claim 2 wherein Xaa$_1$ is His.

7. The compound according to claim 1 wherein Xaa$_2$ is Gly.

8. The compound according to claim 2 wherein Xaa$_2$ is Gly.

9. The compound according to claim 1 wherein Xaa$_3$ is Ala.

10. The compound according to claim 2 where Xaa$_3$ is Ala.

11. The compound according to claim 1 wherein Xaa$_4$ is Ala.

12. The compound according to claim 2 where Xaa$_4$ is Ala.

13. The compound according to claim 1 wherein Xaa$_9$ is Ala.

14. The compound according to claim 2 where Xaa$_9$ is Ala.

15. The compound according to any of claims 8–14 wherein Xaa$_{14}$ is Leu, pentylglycine or Met.

16. The compound according to claim 15 wherein Xaa$_{25}$ is Trp or Phe.

17. The compound according to claim 16 wherein Xaa$_6$ is Ala, Phe or naphthylalanine; Xaa$_{22}$ is Phe or naphthylalanine; and Xaa$_{23}$ is Ile or Val.

18. The compound according to claim 17 wherein the peptide is Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-NH$_2$, (residues 1–28 of SEQ ID NO:4)-NH$_2$.

19. The compound according to claim 17 wherein Xaa$_{31}$, Xaa$_{36}$, Xaa$_{37}$ and Xaa$_{38}$a are independently selected from the group consisting of Pro, homoproline, thioproline and N-alkylalanine.

20. The compound according to claim 1 wherein Xaa$_{39}$ is Ser or Tyr.

21. The compound according to claim 17 wherein Xaa$_{39}$ is Ser or Tyr.

22. The compound according to claim 1 wherein Xaa$_{39}$ is Ser.

23. The compound according to claim 17 wherein Xaa$_{39}$ is Ser.

24. The compound according to claim 1 wherein Z$_2$ is —NH$_2$.

25. The compound according to claim 19, where Z$_2$ is —NH$_2$.

26. The compound according to claim 21, where Z$_2$ is —NH$_2$.

27. The compound according to claim 23, where Z$_2$ is —NH$_2$.

28. The compound according to claim 1 wherein the peptide is Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-NH$_2$, (residues 1–28 of SEQ ID NO:4)-NH$_2$.

29. The compound according to claim 1 wherein Xaa$_{31}$, Xaa$_{36}$, Xaa$_{37}$ and Xaa$_{38}$ are independently selected from the group consisting of Pro, homoproline, thioproline and N-alkylalanine.

30. The compound according to claim 1 which has an amino acid sequence selected from SEQ. ID. NOS. 5 to 93.

31. A peptide compound or pharmaceutically acceptable salt, thereof, selected from:

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Xaa$_{37}$-Xaa$_{38}$-Z$_2$, (residues 1–38 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Xaa$_{37}$-Z$_2$, (residues 1–37 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Ala-Xaa$_{36}$-Z$_2$, (residues 1–36 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Gly-Z$_2$, (residues 1–35 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Z$_2$, (residues 1–34 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Ser-Z$_2$, (residues 1–33 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Ser-Z$_2$, (residues 1–32 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Xaa$_{31}$-Z$_2$, (residues 1–31 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Gly-Z$_2$, (residues 1–30 of SEQ ID NO:4)-Z$_2$;

Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Gly-Z$_2$, (residues 1–29 of SEQ ID NO:4)-Z$_2$; and Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-Xaa$_{27}$-Xaa$_{28}$-Z$_2$, (residues 1–28 of SEQ ID NO:4)-Z$_2$;

wherein:
Xaa$_1$ is His or Ala;
Xaa$_2$ is Gly or Ala;
Xaa$_3$ and Xaa$_{24}$ are each independently Ala, Asp or Glu;
Xaa$_4$ is Ala or Gly;
Xaa$_5$ is Ala or Thr;
Xaa$_6$ is Ala, Phe or naphthylalanine;
Xaa$_7$ is Thr or Ser;
Xaa$_8$ is Ala, Ser or Thr;
Xaa$_9$ is Ala, Asp or Glu;
Xaa$_{10}$ is Ala, Leu or pentylglycine;
Xaa$_{11}$ is Ala or Ser;
Xaa$_{12}$ and Xaa$_{27}$ are each independently Ala or Lys;
Xaa$_{13}$ is Ala or Gln;
Xaa$_{14}$ is Ala, Leu, Met or pentylglycine;
Xaa$_{15}$, Xaa$_{16}$ and Xaa$_{17}$ are each independently Ala or Glu;
Xaa$_{19}$ is Ala or Val;
Xaa$_{20}$ is Ala or Arg;
Xaa$_{21}$ and Xaa$_{26}$ are each independently Ala or Leu;
Xaa$_{22}$ is Phe or naphthylalanine;
Xaa$_{23}$ is Ile, Val or tert-butylglycine;
Xaa$_{25}$ is Ala, Trp or Phe;
Xaa$_{28}$ is Ala or Asn;
Xaa$_{31}$, Xaa$_{36}$, Xaa$_{37}$, and Xaa$_{38}$ are each independently Pro, homoproline, thioproline, N-methylalanine;
Z$_2$ is —OH or —NH$_2$; and
provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and provided also that if Xaa$_1$ is His then at least one of Xaa$_3$, Xaa$_4$ and Xaa$_9$ is Ala.

32. The compound according to claim 31 which has an amino acid sequence selected from SEQ. ID. NOS. 5–9.

33. A composition comprising a compound of any one of claims 1 to 14, 20, 22, 24 and 28 to 31 in a pharmaceutically acceptable carrier.

34. A composition comprising a compound of claim 32 in a pharmaceutically acceptable carrier.

35. A method for the treatment of diabetes mellitus comprising administering to a patient in need thereof a therapeutically effective amount of a compound according to claim 1.

36. A method for the treatment of diabetes mellitus comprising administering to a patient in need thereof a therapeutically effective amount of a compound according to claim 30.

37. A method for the treatment of diabetes mellitus comprising administering to a patient in need thereof a therapeutically effective amount of a compound according to claim 31.

38. The method of claim 35 further comprising administering a therapeutically effective amount of an insulin.

39. The method of claim 36 further comprising administering a therapeutically effective amount of an insulin.

40. The method of claim 37 further comprising administering a therapeutically effective amount of an insulin.

41. A method for the treatment of a hyperglycemic condition in a mammal comprising the step of administering to the mammal a therapeutically effective amount of a compound according to claim 1.

42. A method for the treatment of a hyperglycemic condition in a mammal comprising the step of administering to the mammal a therapeutically effective amount of a compound according to claim 30.

43. A method for the treatment of a hyperglycemic condition in a mammal comprising the step of administering to the mammal a therapeutically effective amount of a compound according to claim 31.

44. A compound or pharmaceutically acceptable salt, thereof, selected from:

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-Ser-Gly-Ala-$Xaa_{36}$-$Xaa_{37}$-$Xaa_{38}$-$Xaa_{39}$-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-Gly-Gly-$Xaa_{31}$-Ser-Ser-Gly-Ala-$Xaa_{36}$-$Xaa_{37}$-$Xaa_{38}$-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-Ser-Gly-Ala-$Xaa_{36}$-$Xaa_{37}$-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-Ser-Gly-Ala-$Xaa_{36}$-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-Ser-Gly-Ala-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-Ser-Gly-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-Ser-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-Ser-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Xaa_{31}$-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-Gly-$Z_2$;

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-Gly-$Z_2$; and $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-Ala-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$X_1$-$Z_2$;

wherein:

$Xaa_1$ is His, Arg, Tyr, Ala, Norval, Val, Norleu or 4-imidazolepropionyl;

$Xaa_2$ is Ser, Gly, Ala or Thr;

$Xaa_3$ and $Xaa_{24}$ are each independently Ala, Asp or Glu;

$Xaa_4$ is Ala, Norval, Val, Norleu or Gly;

$Xaa_5$ is Ala or Thr;

$Xaa_6$ is Ala, Phe, Tyr or naphthylalanine;

$Xaa_7$ is Thr or Ser;

$Xaa_8$ is Ala, Ser or Thr;

$Xaa_9$ is Ala, Norval, Val, Norleu, Asp or Glu;

$Xaa_{10}$ and $Xaa_{14}$ are each independently Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{15}$, $Xaa_{16}$ and $Xaa_{17}$ are each independently Ala or Glu;

$Xaa_{19}$ is Ala or Val;

$Xaa_{20}$ is Ala or Arg;

$Xaa_{21}$ is Ala, Leu or Lys(R),
where R is attached to the ε-amine of lysine and is selected from the group consisting of Lys, Arg, $C_1$–$C_{10}$ straight chain or branched alkanoyl or cycloalkylalkanoyl;

$Xaa_{22}$ is Phe, Tyr or naphthylalanine;

$Xaa_{23}$ is Ile, Val, Leu, pentylglycine, tert-butylglycine or Met;

$Xaa_{25}$ is Ala, Trp, Phe, Tyr or naphthylalanine;

$Xaa_{26}$ is Ala or Leu;

$X_1$ is Lys-Asn, Asn-Lys, Lys(R)-Asn, Lys(R)-Ala, Asn-Lys(R) and Ala-Lys(R),
where R is attached to the ε-amine of lysine and is selected from the group consisting of Lys, Arg, $C_1$–$C_{10}$ straight chain or branched alkanoyl or cycloalkylalkanoyl;

$Xaa_{31}$, $Xaa_{36}$, $Xaa_{37}$, and $Xaa_{38}$ are each independently Pro, homoproline, 3Hyp, 4Hyp, thioproline, N-alkylglycine, N-alkylpentylglcine or N-alkylalanine;

$X_{39}$ is Ser or Tyr;

$Z_2$ is —OH or —$NH_2$; and provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that if Xaa$_1$ is His, Arg, Tyr or 4-imidazolepropionyl, then at least one of Xaa$_3$, Xaa$_4$ and Xaa$_9$ is Ala.

45. The compound according to claim 44 wherein Xaa$_1$ is His, Ala, Norval or 4-imidazopropionyl.

46. The compound according to claim 45 wherein Xaa$_1$ is His or 4-imidazopropionyl.

47. The compound according to claim 45 wherein Xaa$_1$ is Ala.

48. The compound according to claim 45 wherein Xaa$_1$ is His.

49. The compound according to claim 45 wherein Xaa$_1$ is 4-imidazopropionyl.

50. The compound according to claim 44 wherein Xaa$_2$ is Gly.

51. The compound according to any of claims 45–49 wherein Xaa$_2$ is Gly.

52. The compound according to claim 44 wherein Xaa$_3$ is Ala.

53. The compound according to any of claims 45–49 where Xaa$_3$ is Ala.

54. The compound according to claim 44 wherein Xaa$_4$ is Ala.

55. The compound according to any of claims 45–49 where Xaa$_4$ is Ala.

56. The compound according to claim 44 wherein Xaa$_9$ is Ala.

57. The compound according to any of claim 45–49 where Xaa$_9$ is Ala.

58. The compound according to claim 44 wherein Xaa$_{14}$ is Leu, pentylglycine or Met.

59. The compound according to claim 44 wherein Xaa$_{25}$ is Trp or Phe.

60. The compound according to claim 44 wherein Xaa$_6$ is Ala, Phe or naphthylalanine; Xaa$_{22}$ is Phe or naphthylalanine; and Xaa$_{23}$ is Ile or Val.

61. The compound according to claim 44 wherein the compound is Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-X$_1$-NH$_2$.

62. The compound according to claim 44 wherein Xaa$_{31}$, Xaa$_{36}$, Xaa$_{37}$ and Xaa$_{38}$ are independently selected from the group consisting of Pro, homoproline, thioproline and N-alkylalanine.

63. The compound according to claim 44 wherein Xaa$_{39}$ is Ser or Tyr.

64. The compound according to claim 60 wherein Xaa$_{39}$ is Ser or Tyr.

65. The compound according to claim 44 wherein Xaa$_{39}$ is Ser.

66. The compound according to claim 60 wherein Xaa$_{39}$ is Ser.

67. The compound according to claim 44 wherein Z$_2$ is —NH$_2$.

68. The compound according to any of claims 52, 54 or 56 wherein Z$_2$ is —NH$_2$.

69. The compound according to claim 44 wherein the compound is Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$-Xaa$_{14}$-Xaa$_{15}$-Xaa$_{16}$-Xaa$_{17}$-Ala-Xaa$_{19}$-Xaa$_{20}$-Xaa$_{21}$-Xaa$_{22}$-Xaa$_{23}$-Xaa$_{24}$-Xaa$_{25}$-Xaa$_{26}$-X$_1$-OH.

70. The compound according to claim 44 wherein Xaa$_{31}$, Xaa$_{36}$, Xaa$_{37}$ and Xaa$_{38}$ are independently selected from the group consisting of Pro, homoproline, thioproline and N-alkylalanine.

71. The compound according to claim 44 wherein X$_1$ is Lys Asn, Lys-NH$^\epsilon$-R Asn, or Lys-NH$^\epsilon$-R Ala where R is Lys, Arg, C$_1$–C$_{10}$ straight chain or branched alkanoyl.

72. The compound according to claim 44 wherein Xaa$_{21}$ is Lys-NH$^\epsilon$-R where R is Lys, Arg, C$_1$–C$_{10}$ straight chain or branched alkanoyl or cycloalkyl-alkanoyl.

73. The compound according to claim 44 which has an amino acid sequence selected from SEQ. ID. NOS. 95–110.

74. A composition comprising a compound of claim 44 in a pharmaceutically acceptable carrier.

75. A composition comprising a compound of claim 73 in a pharmaceutically acceptable carrier.

* * * * *

UNITED STATES PATENT AND TRADEMARK OFFICE
CERTIFICATE OF CORRECTION

PATENT NO.        : 7,220,721 B1
APPLICATION NO.   : 09/554531
DATED             : May 22, 2007
INVENTOR(S)       : Beeley et al.

It is certified that error appears in the above-identified patent and that said Letters Patent is hereby corrected as shown below:

Column 131, Claim 1, please delete line 2 "salt, thereof, selected from:" and replace it with --salt thereof selected from:--

Column 133, Claim 19, line 2, change "and Xaa38a are" to correctly recite --and Xaa38 are--

Column 133, Claim 31, line 84, change "thioproline, N-methylalanine;" to correctly recite --thioproline, or N-methylalanine--

Column 135, Claim 44, lines 1-2, change "acceptable salt, thereof, selected" to correctly recite --acceptable salt thereof selected--

Signed and Sealed this

Sixth Day of May, 2008

JON W. DUDAS
*Director of the United States Patent and Trademark Office*